US012727927B2

(12) United States Patent
Krause et al.

(10) Patent No.: US 12,727,927 B2
(45) Date of Patent: Sep. 8, 2026

(54) TOOL FOR THE MANIPULATION OF FASTENING DEVICES

(71) Applicants: William R Krause, Charlottesville, VA (US); Daniel W Christensen, Amherst, VA (US)

(72) Inventors: William R Krause, Charlottesville, VA (US); Daniel W Christensen, Amherst, VA (US)

( * ) Notice: Subject to any disclaimer, the term of this patent is extended or adjusted under 35 U.S.C. 154(b) by 677 days.

(21) Appl. No.: 17/652,094

(22) Filed: Feb. 22, 2022

(65) Prior Publication Data

US 2022/0240997 A1 Aug. 4, 2022

Related U.S. Application Data

(63) Continuation-in-part of application No. 17/021,408, filed on Sep. 15, 2020, now Pat. No. 11,253,306, which is a continuation-in-part of application No. 16/818,978, filed on Mar. 13, 2020, now abandoned.

(60) Provisional application No. 62/817,948, filed on Mar. 13, 2019.

(51) Int. Cl.
*A61B 17/16* (2006.01)
*A61B 17/17* (2006.01)
*A61B 17/88* (2006.01)

(52) U.S. Cl.
CPC ...... *A61B 17/8897* (2013.01); *A61B 17/1622* (2013.01); *A61B 17/1717* (2013.01); *A61B 17/8875* (2013.01)

(58) Field of Classification Search
CPC ............ A61B 17/8875; A61B 17/8877; A61B 17/8888
See application file for complete search history.

(56) References Cited

U.S. PATENT DOCUMENTS

| | | | | |
|---|---|---|---|---|
| 8,343,197 | B2 * | 1/2013 | Gonzalez-Hernandez .................. | A61B 17/1728 606/304 |
| 9,482,260 | B1 * | 11/2016 | Krause ................. | A61B 17/869 |
| 11,253,306 | B2 * | 2/2022 | Krause ............... | A61B 17/8888 |
| 11,291,488 | B1 * | 4/2022 | O'Flaherty .......... | A61B 17/864 |
| 11,998,255 | B1 * | 6/2024 | Gregersen .......... | A61B 17/8605 |
| 2020/0289183 | A1 * | 9/2020 | Krause ................ | F16B 25/0005 |
| 2021/0059736 | A1 * | 3/2021 | Kmiec, Jr. .......... | B25B 23/0028 |

* cited by examiner

*Primary Examiner* — Nicholas W Woodall
(74) *Attorney, Agent, or Firm* — Kimberly O Snead

(57) ABSTRACT

A system for manipulating a rotational device using a flexible guide rod with an external rod feature along its length to engage a rotational device with a complementary interior channel feature along its length. A driver having a handle and coupling element is coupled to the rotational device while the flexible guide rod extends from the handle, through the coupling element, and into the interior channel of the rotational device in order to rotate from within along the length of the device.

18 Claims, 26 Drawing Sheets

120
238
200
270
100
220
230
210
150
255
152

121
122
123
125
130
120
A
B
C
D
DETAIL A
SCALE 2 : 1
DETAIL B
SCALE 5 : 1
DETAIL C
SCALE 7.5 : 1
SECTION D-D
SCALE 10 : 1

SECTION B-B
SCALE 2 : 1
212
220
230
222
211
210
B
C
SECTION C-C
SCALE 2 : 1

150
157
156
C
154
158
A

D
E
DETAIL C
SCALE 2 : 1

B
154
158
270
DETAIL A
SCALE 2 : 1

161
125
162
123
160
157
SECTION D-D
SCALE 5 : 1

158
123
155
272
122
270
SECTION B-B
SCALE 5 : 1

159
166
123
DETAIL F
SCALE 50 : 1

157
160
159
166
123
F
SECTION E-E
SCALE 10 : 1

150
154
G
G 154
172
171
174

SECTION G-G
SCALE 8:1
H 171
174
172
Parallel
DETAIL H
SCALE 16:1

270
272
274
SECTION A-A
270
274
272

274
A
A
270

410
402
406
414
B
B 420
410
C
SECTION B-B
SCALE 16 : 1

410
412
Gap
405
404
420
DETAIL C
SCALE 64 : 1

500
504
515
501
502

500
D
C 500
501
SECTION C-C
SCALE 4 : 1

510
501
502
500
SECTION D-D
SCALE 1.5 : 1

560
550
FLAT ALIGNMENT SIDE
D
D
B
B
C
C
566
556
555
SECTION D-D
SCALE 4 : 1
SECTION C-C
SCALE 8 : 1
SECTION B-B
SCALE 8 : 1

575
576
573
FLAT
577
570
572
574

587
586
580
584
582
588
585
583

600
A
A

C
C
D
D
E
SECTION A-A
SCALE 1:1.5
575
150
SECTION D-D
SCALE 6:1

174
SECTION C-C
SCALE 6:1

588
576
155
580
570
DETAIL E
SCALE 2:1

TOOL FOR THE MANIPULATION OF FASTENING DEVICES

FIELD OF THE INVENTION

The present invention pertains to flexible shafts, fastening devices and a tool assembly and system for manipulating rotational devices, such as screws and reamers.

BACKGROUND

The application of flexible fastening devices encompasses a broad spectrum of industries, included, but not limited to, manufacturing, construction, mining, transportation, agriculture, aviation, automotive, and medical. Flexible fastening devices, either tipped like screws or flat end like bolts, have the characteristics of the cylindrical portion of the device being bendable about the longitudinal length. Flexible fastening devices are useable in many applications, from manufacturing to medical, to secure two objects together.

In numerous industries, flexible fastening devices are used to join curved members together, to join misaligned holes, to absorb vibration between two components, and numerous other applications. In addition, flexible devices are used to connect two or more members whereby a straight passage of the bolt is impossible and a curved passage in one member allows the inserted flexible screw or bolt to follow the passage and be joined to another member. For example, two curved tubes can be connected by inserting a flexible bolt through the internal diameter of one to thread into the internal diameter of the other tube to join them together.

In the medical industry, particularly in orthopedics, flexible screws are particularly useful in the intramedullary fixation of fractured or severed bone fragments. Bone screws are typically used as internal fixation to anchor the fixation system to the relevant bone portions or to join two or more fragments of a fractured bone into close proximity for bone union. For example, screws can be used in plate or rod systems to treat complex fractures of long bones or conditions such as vertebral instability. In small bone fractures, such as the bones of the hands, feet, and wrist, the screw is placed across the fracture site to bring the fracture surfaces in close proximity. In medium (clavicle, rib and others) and long (lower and upper extremities) bone fractures, screws can be inserted into the intramedullary canal for minimally invasive fracture reduction.

Various surgical procedures utilize devices to fixate anatomical tissue for healing. An example of a fixation device is a compression bone fixation screw, or compression screw, used to fixate two or more bone fragments or intramedullary fixation of a bone.

Typically, a guide wire is inserted through the fractured bone to align the fragments and provide a path for canal enlargement tools and the screw to follow. A surgical screwdriver or insertion tool having a drive shaft for rotating the screw and advancing it along the inserted guide wire is commonly used to insert bone screws. The driver cooperatively engages with a drive recess, within the proximal end of the screw, to help achieve axial alignment of the screw with the drive shaft of the screwdriver. Improvement of fastening devices and insertion tools is needed to prevent rotation of the screwdriver with the guide wire over which the screw is placed.

SUMMARY OF THE INVENTION

A system for manipulating a rotational device such as a screw, compression screw, or reamer using a flexible guide rod with an external rod feature along its entire or partial length to engage a rotational device with a complementary interior channel feature along its length is disclosed. A driver having a handle and coupling element is coupled to the rotational device while the flexible guide rod extends from the handle, through the coupling element, and into the interior channel of the rotational device in order to rotate from within along the length of the device, thus avoiding twisting of the rotational device. The flexible guide rod has a distal section, mid-section, and proximal threaded section. The rotational device has an exterior, a distal end, and an open interior channel. The open interior channel has a distal section, mid-section, and proximal section. The distal section of the interior channel has a periphery greater than or equal to the periphery of the distal section of the flexible guide rod and is dimensioned to receive the periphery of the proximal section of the flexible guide rod. The periphery of the proximal section of the interior channel periphery is configured to receive a driver coupling element. The external rod feature extends along at least a portion of the mid-section and proximal threaded section of the guide rod to interact with the complimentary interior channel feature of the rotational device. The periphery of the interior channel mid-section interacts with the periphery of the guide rod mid-section and secures the distal section of the guide rod within the distal section of the interior channel at a transitional point once the guide rod is received by the distal section of the interior channel.

The disclosed system can use any complementary external rod feature and interior channel feature that allows minimum rotation and prevents complete rotation, preferably less than 10 degrees, of the guide rod within the channel of the rotational device. The preferred complementary configuration of the features is a flat to form a D-shape and where the flat is between 25 to 75 percent of a radius of said guide rod.

BRIEF DESCRIPTION OF THE DRAWINGS

The objects, features, advantages and aspects of the present invention can be better understood with reference to the following detailed description of the preferred embodiments when read in conjunction with the appended drawing figures. All of the figures are drawn on an oversized scale, and like structure in different figures bears like reference numerals.

FIG. 9A is a side view of the handle subassembly 200 of FIG. 8 illustrating the section lines B-B and C-C in accordance with the invention;

FIG. 9B is the detailed view of Section B-B in FIG. 9A in accordance with the invention;

DETAILED DESCRIPTION OF THE INVENTION

Definitions

Figure 1:
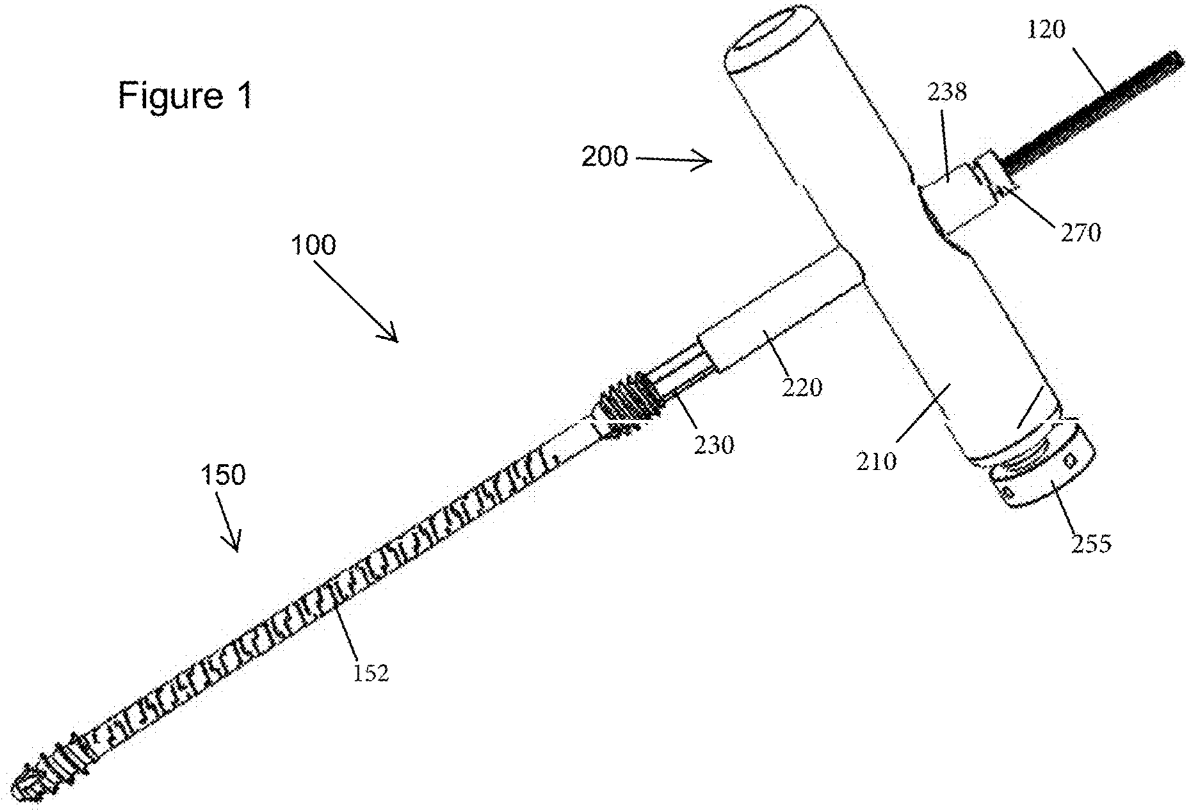
FIG. 1 is a perspective view of the tool assembly 100 with screw 150 and attached handle sub-assembly 200 in accordance with the disclosed invention.

As used herein the term "about" shall refer to plus or minus ten percent (10%).

As used herein the terms "fastening device", "flexible rotating shaft", "flexible device", "screw", and "bolt" shall be used interchangeably and reference any flexible device that can secure two or more objects together.

As used herein the term "manipulation" or "manipulating" shall refer to inserting, removing, tightening, loosening, or adjusting of a screw; the terms "manipulation" or "manipulating" can be used interchangeably with "drive" or "driving" or "driven".

As used herein the term "compression fastening device" shall refer to any flexible device that can secure two or more objects together and tighten the contact through causing the fastening device to shorten.

As used herein the term "complimentary configuration" will mean shapes of interacting parts that interact with one another to prevent rotation of interacting parts individually.

As used herein the term "distal" shall refer to situation closer to the point of interaction between the tool assembly and an intended element.

As used herein the term "proximal" shall refer to situation farther away from the point of interaction between the tool assembly and an intended element.

As used herein the term "element" shall refer to any object or objects requiring the manipulation of a screw.

When driven devices such as screws, drills, reamers, and shafts are rotated, an angular deformation of the device will result; and if rotated beyond a given point, the device will permanently deform or catastrophically fail. This is particularly characteristic of devices that are manufactured to be flexible.

In a medical environment, the use of flexible devices, such as bone screws, reamers, screw drivers, and other instruments that require rotation is hindered by the twisting of the device when manipulated by the proximal end. In addition, broken devices within an element are also a problem and a mechanism or tool is needed to remove the portions of the broken device.

Physical features can be incorporated into these rotationally driven devices that are unique and novel to prevent the excessive rotation of the device which would result in deformity or breakage of the device. In addition, advanced manufacturing processes can be utilized to incorporate the features into the device.

The features incorporated into the flexible devices such as, but limited to, screws, reamers, screw drivers and other flexible instrument shafts include an interior shape or cross section that is complimentary to an inserted guide rod.

The use of flexible devices, such as bone screws and reamers, that require rotation is hindered by the twisting of the device when manipulated by the proximal end. In addition, broken devices within an element are also a problem and a mechanism or tool is needed to remove the distal portion of a broken screw. In the present invention, the screwdriver or insertion tool has means of preventing rotation of the screwdriver with the guide wire over which the screw is placed.

It has been determined that in a device having an interior cavity or channel, if the interior cavity of the device has a shape that is complimentary to the shape of a guide rod and is non-circular, and the guide rod can be inserted into the cavity from the distal end, the screw can then be driven from both the driver receiving area at the proximal end and the interior channel. In this way, the screw can be inserted, removed, tightened, loosened, or otherwise adjusted as needed by application of rotary force along the length of the body or a section within the interior of the device. This is especially applicable when the device is flexible and can be in a curved orientation, such as a bone cavity, through which the rod must pass to enter the distal end of the screw. The ideal choice of material for the guide rod portion of this application is Nitinol, a nickel-titanium alloy, although other metallic alloys or flexible polymers and composites meeting the criteria set forth herein are applicable.

The rod can also be used to insert the screw. Thus, when coupled with a driving attachment to the proximal end of the screw, the driver would be applying the driving torque to both the proximal end and the length of the screw, thus relieving the twisting of the central flexible segment of the screw. Although the insertion rod and internal complimentary shaped internal cavity are shown as "D-shaped", any complimentary shapes that do not allow rotation relative to one another are applicable.

Similarly, removal of a screw using the interior channel also facilitates removal when the screw, or device, is broken. When inserted into the interior channel, the complimentary rod can be used to rotate the screw in the opposite direction from insertion, resulting in the screw backing itself out. Although it is common to back out a non-flexible screw, flexibility and screw length have prevented this from being easily accomplished heretofore.

The D-shape disclosed herein as the complimentary shape provides maximized thread area for the locking nut in addition to increased contact between the length of the guide rod and the entire length of the fastener. These D-shape features prevent angular deflection along the length of the fastener during insertion or removal. In addition, it is easier to manufacture the D-shape, on one for both sides of the rod, in a wide variety of lengths than many other complimentary shapes.

The distal end of the fastener and the distal end of the guide rod must both have complimentary configurations that maintain the distal end of the guide rod at the distal end of the fastener in order to compress the fastener if necessary. This can be accomplished in a number of methods and beyond those mentioned herein will be known to those skilled in the art.

In the description herein interior cross section will have a "D" shaped periphery although other shapes, such as a multi-sided (but limited to a 2-sided, hex, square, octagon, elliptical) configuration would accomplish the same purpose; to prevent rotation of the guide rod with the device.

The interior distal end of the of the fastener can have a recess that can be a slight taper of 1-2 degrees to receive the complimentary distal tip of the guide rod. Thus, when the fastener is fully inserted to the end of the guide rod and the bone, the insertion tool is removed and the locking nut is screwed down to the fastener distal end, the nut draws the distal tip of the guide rod into the distal end of the fastener, compresses the fastener and stiffens it. After the nut has been tightened, the guide rod is cut off proximal to the nut.

Although the tapered end of the guide rod can be produced as part of a single rod, it can increase the cost depending on the material of manufacture. To reduce cost, the guide rod can have a consistent diameter and a tapered tip welded onto the distal end. This can be accomplished more easily by having a sleeve 161 (FIG. 12A) secured over the distal end to provide reinforcement and to provide a smooth surface.

Alternatively, the guide rod distal tip can have an untapered diameter or bulb end slightly larger than the body of the guide rod. In one instance, the interior distal end of the fastener would have an interior dimension equal to that of the guide rod distal tip with the diameter of the interior body of the fastener being dimensioned to receive the body of the guide rod. This would form a "step" that when inserted from the distal end, the guide rod tip would be prevented from entering the interior channel of the fastener by the step produced by the change in interior diameters. In another instance, the distal tip is larger than the diameter of the outer size of the fastener. Both instances, the distal tip would prevent the fastening device from being driven past the end of the guide rod. A distal tip of the guide rod having a diameter equal to or less than the interior diameter of the distal section of the fastening device would allow removal of the guide rod while leaving the fastening device in place if the situation warranted. In another instance the guide rod distal tip is absent, and the guide rod can be removed from the fastening device after insertion into the bone or mating parts.

In prior art devices the alignment of the guide rod with the distal internal mating cavity and the mating cavity on the handle was dependent upon the alignment of the internal driving cavity at the distal end of the screw which receives the complimentary shaped driving coupling mechanism on the driver. This prior art approach made it more difficult to align all of the elements and requires additional instrumentation. This problem is eliminated in the disclosed system by having a separate element that is complimentary to the shape of the guide rod and is initially allowed to rotate freely but locks in place for driving the screw when necessary. In addition, other improvements have been incorporated into the design to ease manufacturing.

The embodiment illustrated in FIG. 1 shows the tool assembly 100 illustrating the handle sub-assembly 200 and attached fastening device 150 in accordance with the disclosed invention for the manipulation of screws such as insertion, removal, tightening, loosening, or other adjustment. The handle sub-assembly 200 in combination with the guide rod 120 enables the manipulation of both flexible, as well as inflexible, screws. The handle sub-assembly 200 comprises a handle 210, a handle shank 220, a coupling mechanism 230, guide rod holder clamp 250, guide rod holder clamp screw 255, and a guide rod holder 238. The coupling mechanism 230 has an external configuration to interact with the proximal end of the intended fastening device 150 as well as an internal configuration to interact with the proximal end of the guide rod 120. The locking nut 270 is also illustrated in this figure although its use is optional and would generally be used after removal of the handle sub-assembly.

Figure 2:
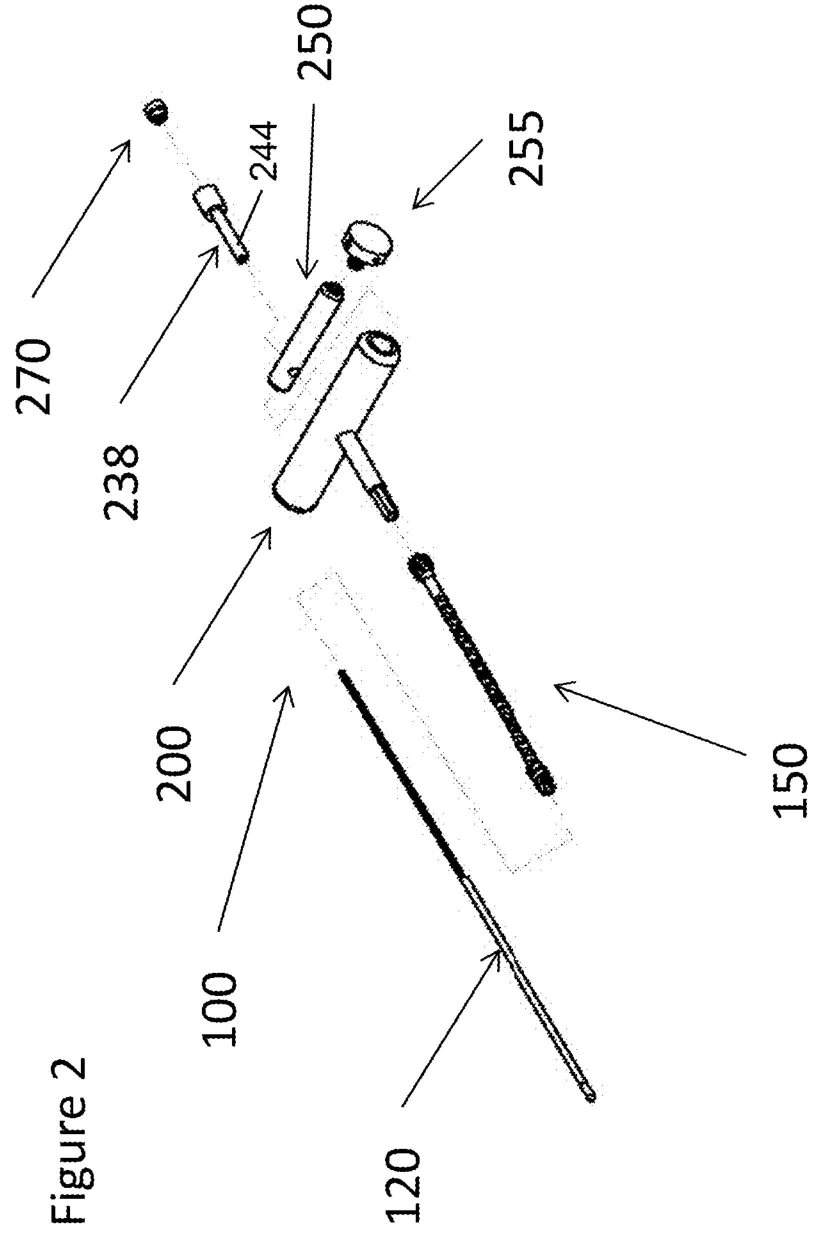
FIG. 2 is an exploded view of the tool assembly 100 prior to insertion of the guide rod in accordance with the invention.

As illustrated in FIG. 2, the guide rod sub-assembly 110 is composed of the guide rod 120 and fastening device 150 that are attached to the handle sub-assembly 200. When attached, guide rod 120 is secured within the handle sub-assembly 200 by the guide rod holder 238 and guide rod holder clamp 250 while fastening device 150 is secured to the handle sub-assembly 200 by coupling mechanism 230. The coupling mechanism 230 has an external configuration to interact with the proximal end of the intended fastening device 150. Locking nut 270 secures the guide rod 120, after removal of the handle sub-assembly 200, with the fastening device 150 to tighten the fastening device 150 with the guide rod 120.

Figures 15A, 15B, 15C, 16A, 16B, 17A, 17B:
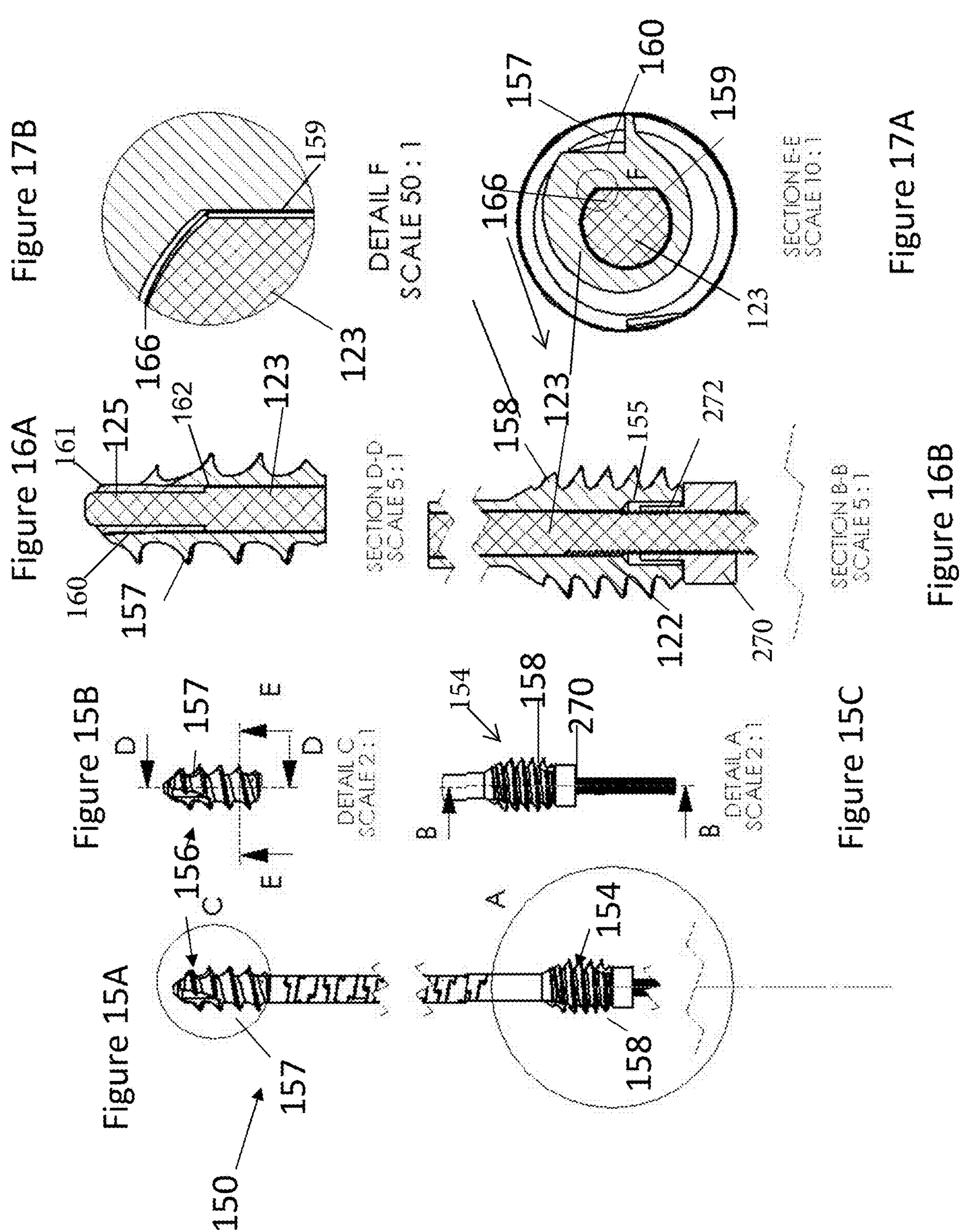
FIG. 15A illustrates the fastening device 150 with the locations of sections E and D indicated in accordance with the invention.
FIG. 15B illustrates the distal end of the fastening device 150 with the locations of sections A and C indicated in accordance with the invention.
FIG. 15C illustrates the detailed section A of the fastening device 150 with the location of section B indicated in accordance with the invention.
FIG. 16A illustrates a cutaway of the distal end of the fastening device 150 in accordance with the invention.
FIG. 16B illustrates a cutaway of the proximal end of the fastening device 150 in accordance with the invention.
FIG. 17A is a cross-sectional view of the fastening device 150 along section E-E of FIG. 11B in accordance with the invention.
FIG. 17B is a cross-sectional view of the gap between the guide rod 120 and the fastening device 150 in accordance with the invention.

For descriptive purposes the guide rod 120, although used as a single rod, is being referenced as three sections, proximal threaded section 121, mid-section 123, and tapered end section 125 as illustrated in FIGS. 3-7. Each of the sections 121, 123, and 125 have a periphery and diameter. The periphery of distal section 125 is greater than the periphery of proximal section 121 and mid-section 123. The rotational device has an exterior, a distal end, and an open interior channel. The open interior channel has a distal section, mid-section, and proximal section. The distal section of the interior channel has a periphery greater than or equal to the periphery of the distal section of the flexible guide rod and is dimensioned to receive the flexible guide rod. The periphery of the proximal section of the interior channel periphery is configured to receive the coupling mechanism. For the purpose of illustration, the guide rod 120 has a D-shaped cross-sectional shape (FIG. 7) extending along at least a portion of the mid-section 123 and proximal threaded section 121 to interact with the complimentary interior channel surface 159 (FIG. 17A) of the fastening device 150. The length of the mid-section 123 of the guide rod must be less than the length of the fastening device 150 to enable the locking nut 270 to be screwed down to contact the proximal end of the screw 154 (FIG. 15C). Alternatively, the entire length of the guide rod 120, with the exception of the distal end section 125, can be threaded. Whether threading the entire length or only a portion of the length will be dependent upon materials of manufacture and end use. When having a non-threaded rod, a rod clamp can be substituted for the locking nut to secure the rod 120 to the fastener 150.

Figures 3, 4, 5, 6, 7:
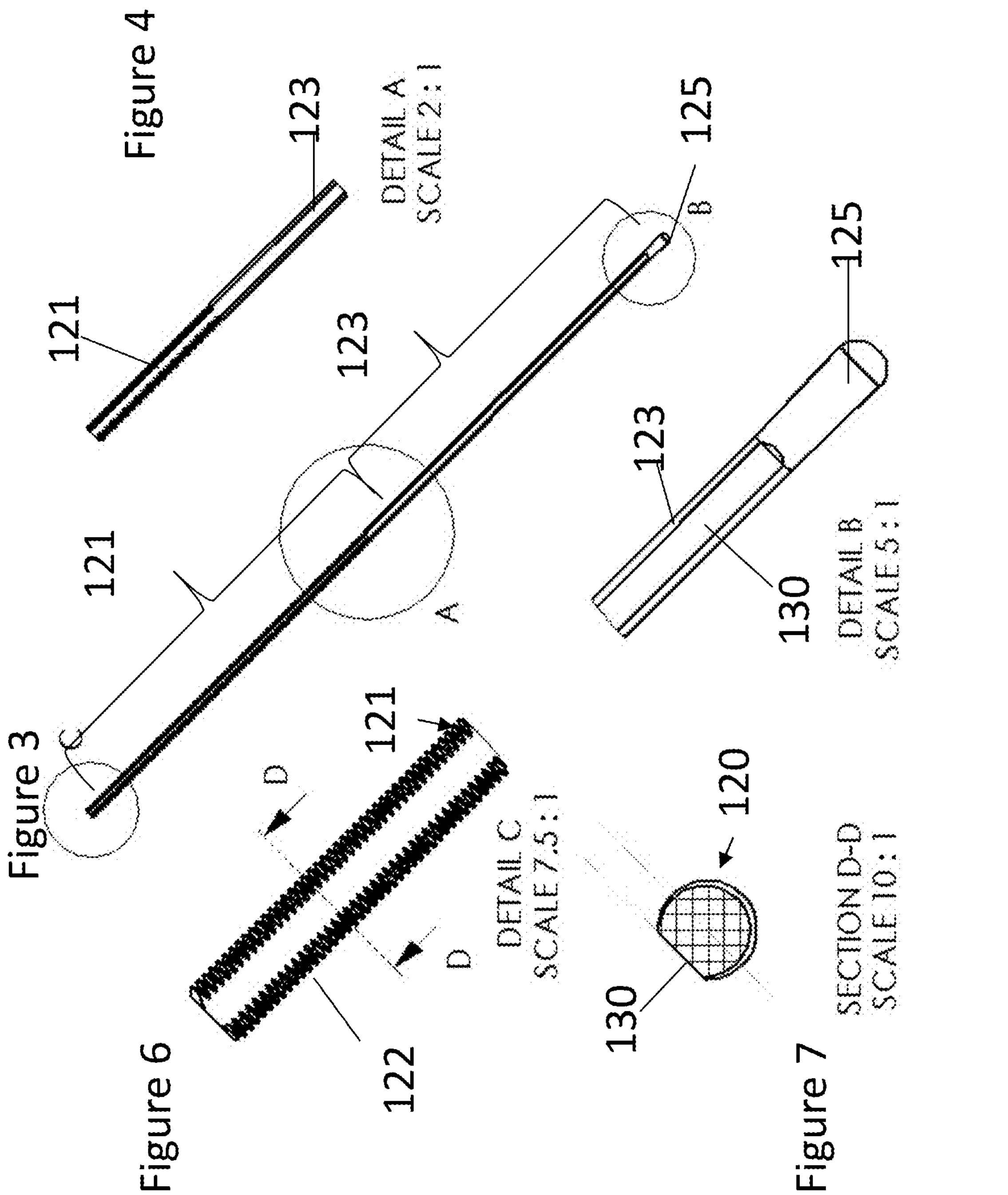
FIG. 3 is a longitudinal view of the guide rod 120 showing locations of the detailed views A, B, and C, in accordance with the invention.
FIG. 4 is a longitudinal view of detail section A of the guide rod 120 transition between threaded section 121 and unthreaded section 123, in accordance with the invention.
FIG. 5 is a view of detail section B of the guide rod 120 illustrating the tapered distal end 125, unthreaded section 123 and D-shape forming flat 130, in accordance with the invention.
FIG. 6 is a view of detail section C of the guide rod 120 illustrating the threads 122 of the threaded section 121 and the location of D-D, in accordance with the invention.
FIG. 7 shows the cross-sectional shape of the D-shaped guide rod 120 at section D-D in accordance with the invention.

The guide rod 120 illustrated in Detail A of FIG. 4 illustrates the area between the threaded proximal section 121 and the mid-section 123.

FIG. 5 illustrates the detail B showing the flat 130 of the D-shaped mid-section 123 and the end of the flat 130 at the juncture of the mid-section 123 and the tapered end section 125. The tapered end section 125 as illustrated is tapered about 1 to 2 degrees to engage the tip of the fastening device as described hereinafter. If the tapers are not dimensioned such that the end section 125 is prevented from movement along the interior channel 159, the guide rod 120 will be free to move toward the proximal end of the fastener 150 upon tightening of the locking nut 270. As stated herein, the tightening of the lock nut 270 pulls the distal end of the fastener 150 toward the proximal end, compressing the fastening device 150 and thereby pulling the objects being secured tighter together.

FIG. 6 is a detailed view of the fine threads 122 of the guide rod proximal threaded portion 121 of the guide rod 120. The thread size used is appropriate for the diameter or shape of the rod as known in the art.

Figures 19, 20, 21:
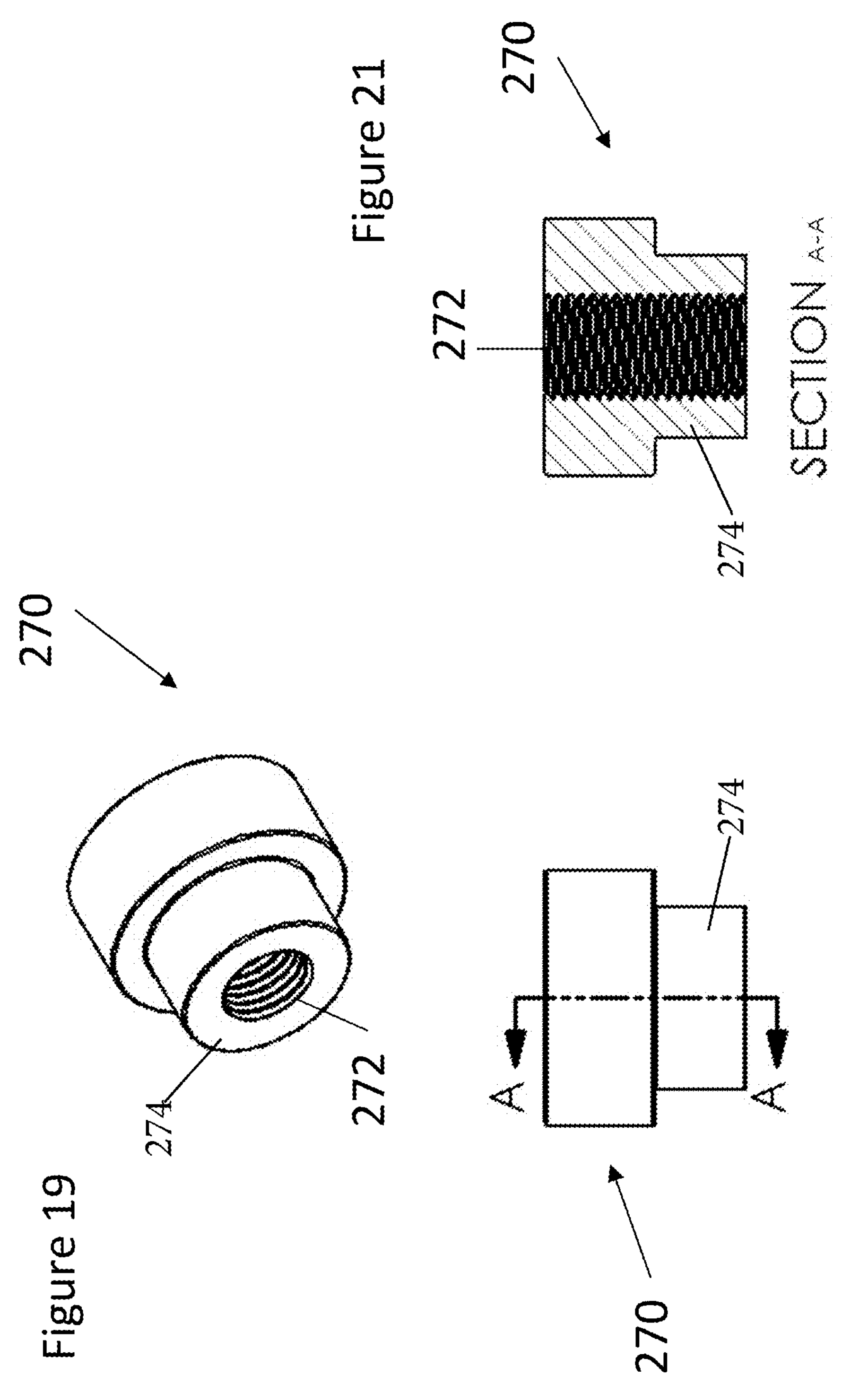
FIG. 19 is a perspective view of the locking nut 270 in accordance with the invention.
FIG. 20 is a side view of the locking nut showing section A-A in accordance with the invention.
FIG. 21 is a cutaway of the locking nut of FIG. 18 illustrating the threaded section A-A in accordance with the invention.

FIG. 7 illustrates the cross-section of the D-shape used herein for both the guide rod 120 and the interior channel 159 of the fastener 150 or rotating device, such as the reamer of FIG. 21. The portion of the guide rod 120 that forms the flat 130 is dependent upon the diameter of the guide rod 120 which in turn is dependent upon the end use. Typically, the flat would be located between 25 to 75 percent of the radius of the rod's diameter as measured from the center. Changes to this percentage can vary in some end uses that will be known to those skilled in the art.

Although a single flat 130 is illustrated and referenced herein, opposing sides of the guide rod can have flats or other unique and complimentary shapes. More than a single flat, as well as how much of the guide rod is removed, can compromise the integrity of the guide rod. The point at which integrity will be compromised depends on the materials being used and the end use and will be known by those skilled in the art.

Figure 8:
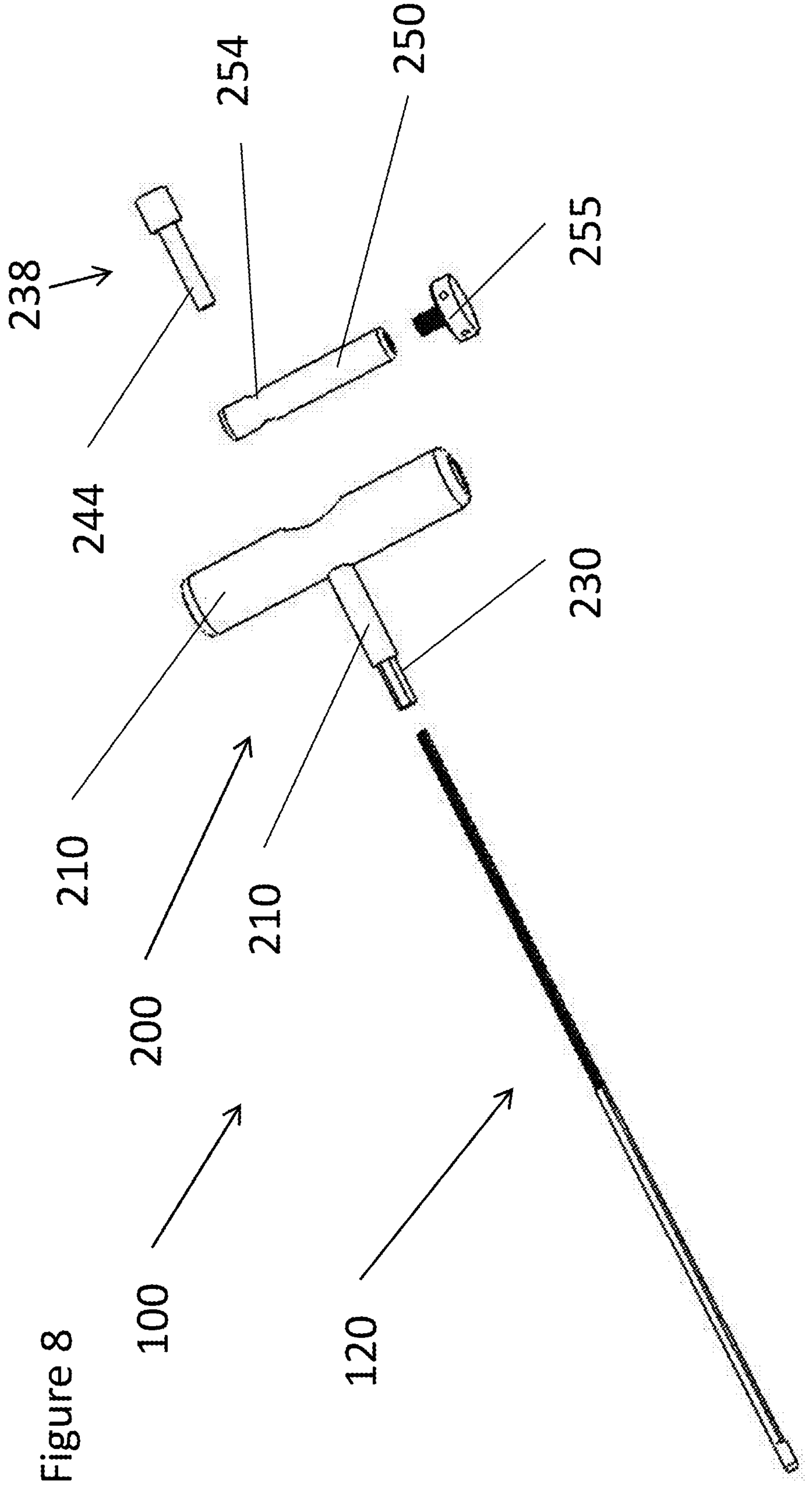
FIG. 8 is an exploded view of the handle subassembly 200 in accordance with the invention.
Figures 9, 9C:
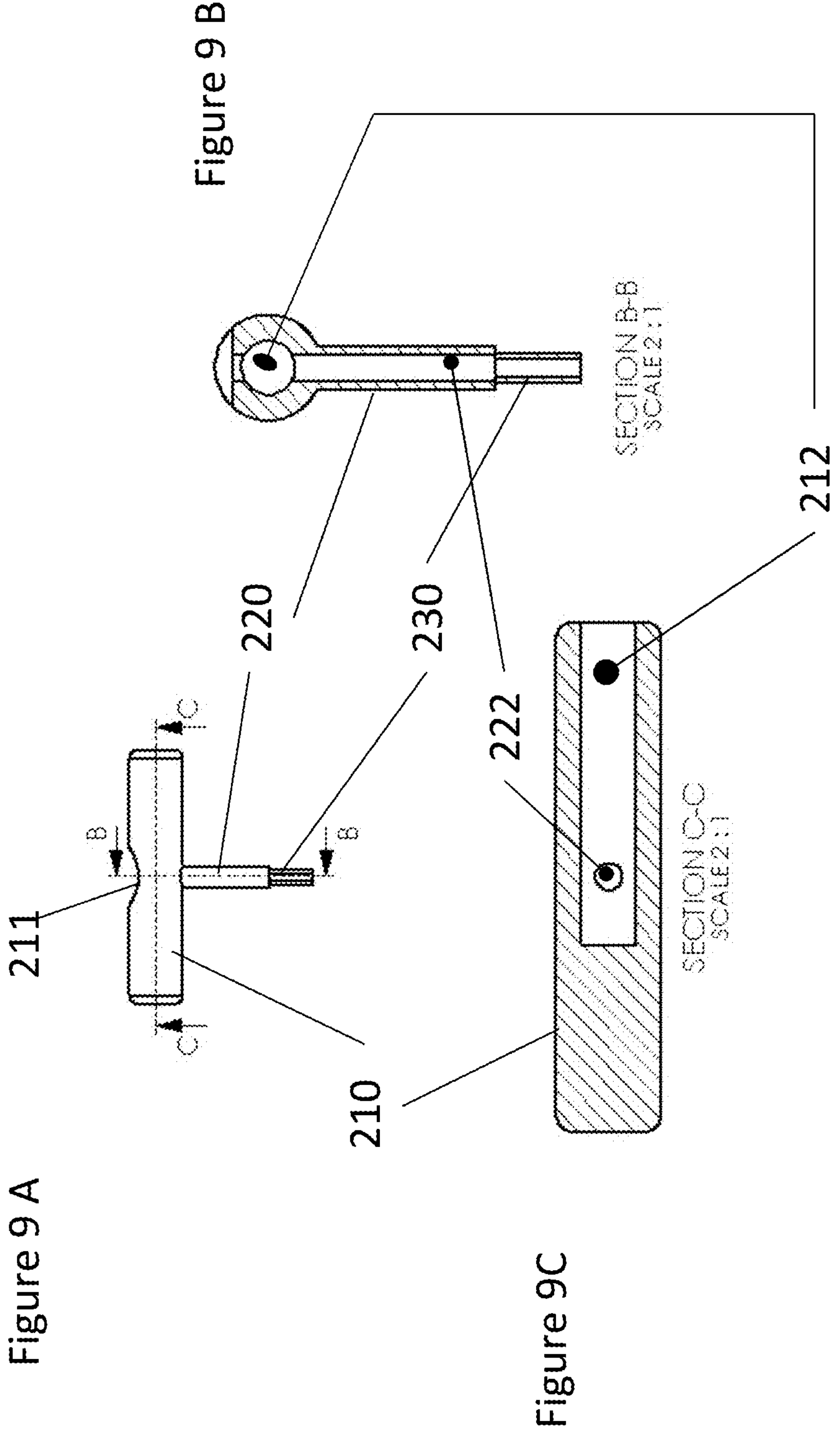
FIG. 9C is the detailed view of Section C-C in FIG. 9A in accordance with the invention.
Figures 9D, 9E, 9F:
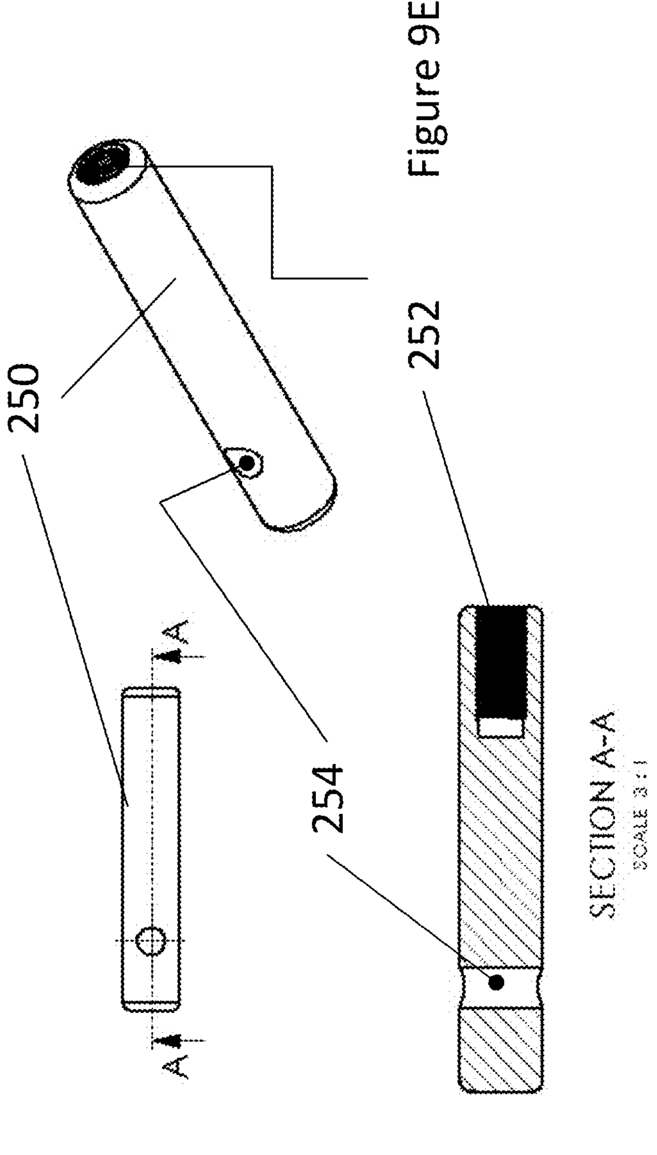
FIG. 9D is a top view of guide rod holder clamp 250 and location of Section A-A.
FIG. 9E is an isometric view of the guide rod holder clamp 250.
FIG. 9F is the sectional view A-A of the guide rod holder clamp 250.

FIG. 8 illustrates an exploded view of the guide rod 120 inserted into the coupling mechanism 230 of the handle sub-assembly 200, through the handle shank 220 and exiting the handle 210. To maintain the guide rod 120 in position during insertion of the fastening device 150, the guide rod 120 is locked into position by the guide rod holder clamp 250 in combination with the guide rod holder 238.

As illustrated in FIGS. 9A-9F and described in more detail in co-pending application Ser. No. 17/021,408, the guide rod holder clamp 250 (FIG. 9D-F) is inserted in clamp orifice 212 in the handle 210 such that the circular guide rod hole 254 is aligned with the circular guide rod shank passage 222 shown in FIGS. 9B and 9C of the handle shank 220. This alignment is necessary so that the guide rod holder shaft 244 can be inserted through holder shaft receiving area 211 into the guide rod shank passage 222. Guide rod stop end 240 of the guide rod holder 238 prevents the guide rod holder 238 from passing through the passage. The clamp screw threads 257 of the guide rod holder clamp screw 255 are inserted into the internal threads 252 of the guide rod holder clamp 250. The guide rod holder clamp screw 255 is used to secure the guide rod holder shaft 244 of guide rod holder 238 in a stationary position within the guide rod shank passage 222 when it is inserted through the holder shaft receiving area 211 within the insertion handle 210. Prior to engagement of the guide rod holder clamp screw 255, the guide rod holder 238 is free to move within the passage. Although the use of a guide rod holder clamp screw 255 engaging with the threads 252 within the guide rod holder clamp 250 is an easy to manufacture method of preventing movement of the guide rod 120, other methods as known in the art can be used.

It is critical during the procedure that the guide rod shank passage 222 and the guide rod hole 254 can be aligned so the guide rod holder shaft 244 can be inserted through the guide rod holder clamp 250. After the guide rod 120 is inserted, the threading of the guide rod holder clamp screw 255 draws the guide rod holder clamp 250 outwards relative to the insertion handle 210 thus locking the holder shaft 244 in place relative to the handle sub-assembly 200 and the screw 150. If it is desired to allow the rod to rotate relative to the handle sub-assembly 200 and the screw 150, the holder clamp 250 would not be tightened.

Figure 12:
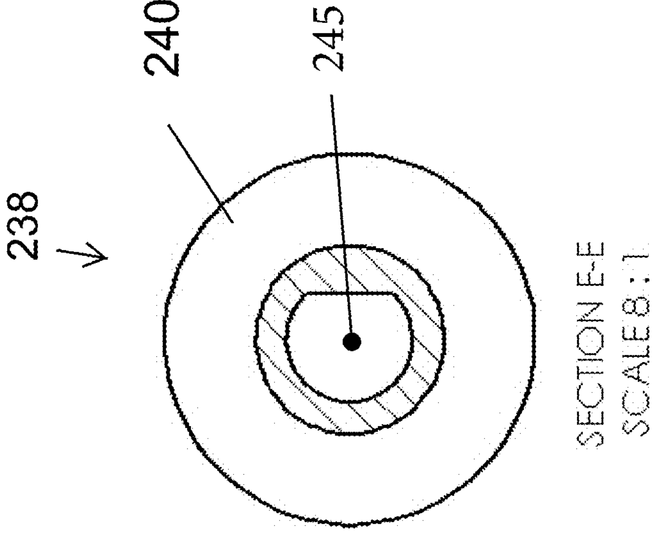
FIG. 12 is a cutaway side view of the guide rod holder 238 along section E-E in accordance with the invention.
Figure 11:
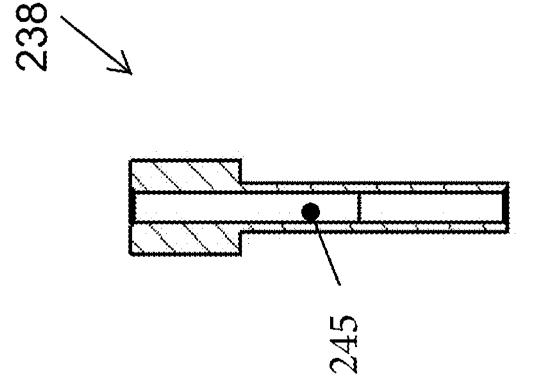
FIG. 11 is a cutaway side view of the guide rod holder 238 along section D-D in accordance with the invention.
Figure 10:
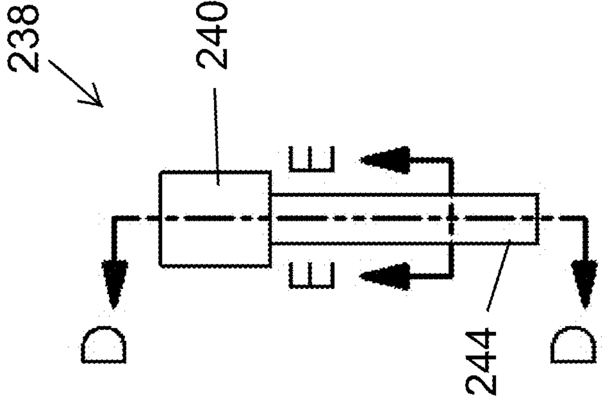
FIG. 10 is a side view of the guide rod holder 238 illustrating sections D-D and E-E in accordance with the invention.
Figure 13:
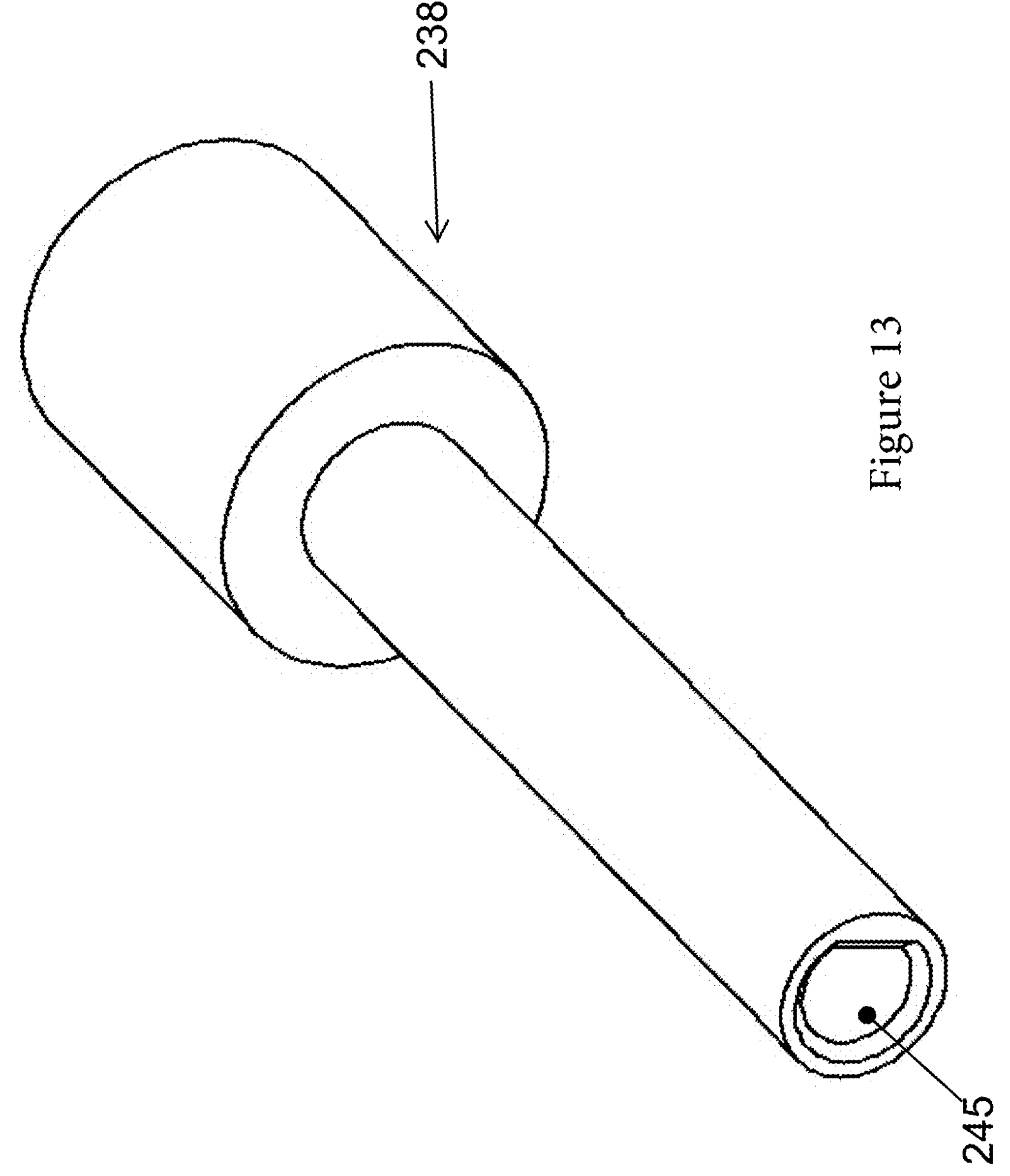
FIG. 13 is a perspective view of the guide rod holder 238 in accordance with the invention.

FIG. 10 illustrates the side view of the guide rod holder 238, comprising the guide rod holder stop end 240, holder shaft 244, and the locations of sectional views D-D, and E-E. Longitudinal section D-D is shown in FIG. 11 illustrating the guide rod shaft passage 245 within holder shaft 244 and coupling mechanism 230 for the passage of the guide rod 120 through the guide rod holder 238. The interior shape of the holder shaft 244 and thus the shape of guide rod shaft passage 245 is D-shaped as shown in FIG. 12 of Section E-E. The guide rod holder 238 is illustrated in FIG. 13 illustrating the D-shaped guide rod shaft passage.

The interior passages of the handle sub-assembly 200, with the exception of the guide rod holder 238, are all circular. The circular configuration enables the guide rod holder 238 to rotate unobstructed within the handle sub assembly 200 until the guide rod 120 is aligned with the D-shape configuration of the screw 150. Once the guide rod shank passage 222 and the guide rod hole 254 are aligned so the guide rod holder shaft 244 can be inserted through the guide rod holder clamp 250, the guide rod holder 238 is inserted, with the D-shaped configuration of the guide rod shaft passage 245 matching the D-shaped configuration of the interior channel of the screw 150.

Figure 14:
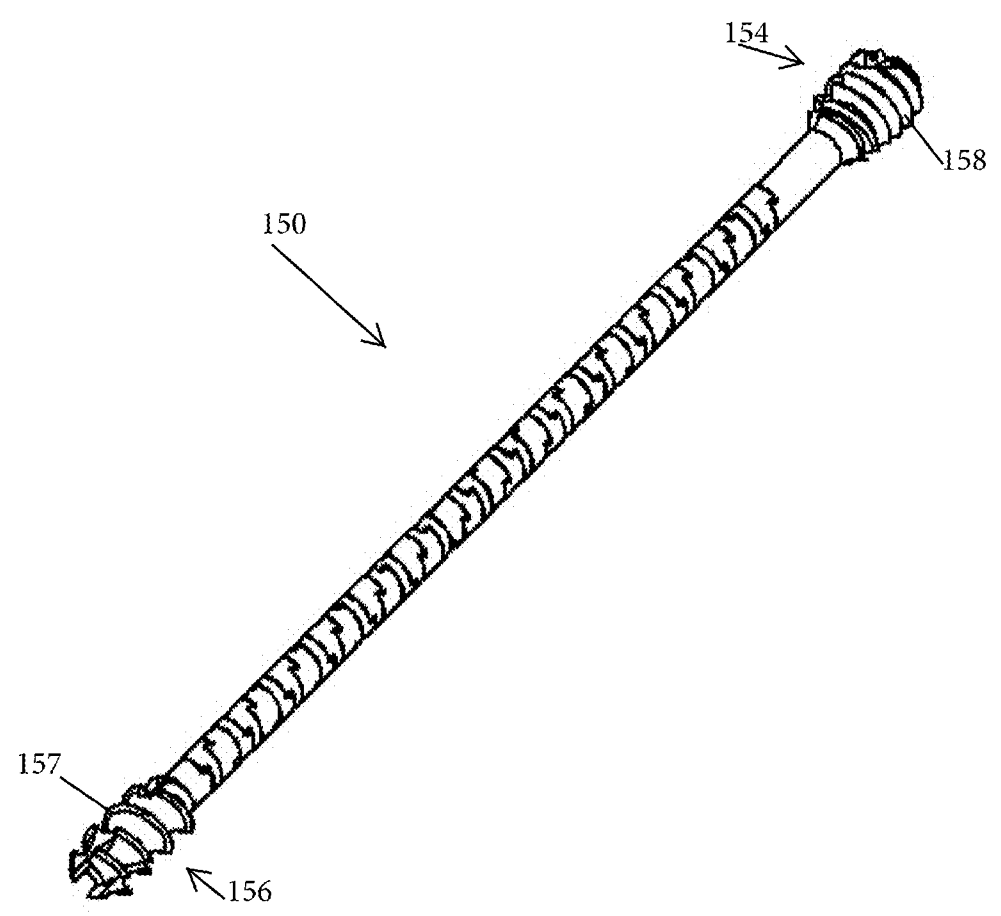
FIG. 14 illustrates an example fastening device 150 incorporating the D-shaped interior in accordance with the invention.

FIG. 14 illustrates the example fastening device 150, more detail and the interior of which are illustrated in FIGS. 16A-B and 17A-B. The exterior of the fastening device 150 can take a number of configurations in length, width, and flexibility, and the example illustrated in FIG. 14 is for example only.

The fastening device 150 is illustrated in more detail in FIGS. 15A-17A wherein FIG. 15A illustrates the fastening device 150, in this example a compression screw the flexible design of which is as described by Krause U.S. Pat. No. 9,482,260, with its proximal segment 154 containing proximal threads 158, distal segment 156 with distal threads 157, and central flexible segment 152 there between. Although the central segment illustrated herein is flexible, the interior configuration would remain the same for non-flexible devices. In FIG. 15B the distal end 154 of the fastening device 150, indicated as Detail C, is illustrated. In this figure the locations of sections D-D and E-E as referenced in FIGS. 16A and 17A are identified. FIG. 15C illustrates the proximal end 154 showing the threads 158 and the locking nut 270 adjacent the proximal end 154. The location of B-B as illustrated in FIG. 15C is also provided. In FIG. 16B the threaded section 122 and the mid-section 123 of guide rod 120 are illustrated positioned within the proximal end of the fastening device 150. Also illustrated is the locking nut 270 (FIGS. 18-20) and its threads 272 abutting the proximal end of the fastening device 150. As noted previously, the flexible guide rod 120 has a distal section, mid-section, and proximal threaded section, with the mid-section and proximal section having like peripheries that are less than the periphery of the distal section. The distal section of the interior channel has a periphery at least the size of the periphery of the distal section of the flexible guide rod and is dimensioned to receive the flexible guide rod. The periphery of the proximal section of the interior channel periphery is configured to receive driver coupling element.

FIG. 16A provides a detailed view of the tapered internal distal section D-D dimensioned to receive the distal tapered section 125 that couples with the internal distal end 160 of fastening device. In this figure the sleeve 161 is used to form the taper to the tapered end section 125. The use of the sleeve 161 as a method of creating a taper is described heretofore. The internal diameter of the fastening device 150 changes at the internal change or transitional point 162, reducing the diameter to that of the tapered internal distal end 160 to the internal channel 159 and changing the configuration of the D-shaped internal channel 159. This internal change point 162 also serves, in addition to the tapered configurations, to lock the guide rod 120 in place. As the tapered end section 125 is not used to rotate the fastening device 150, the cross-sectional shape is preferably round for ease of manufacturing, however other shapes can be used. The periphery of the interior channel mid-section secures the distal section of the guide rod within the distal section of the interior channel at a transitional point once the guide rod is received by the distal section of the interior channel.

As the tapered end section 125 is not used to rotate the fastening device 150, the cross-sectional shape is preferably round for ease of manufacturing, however other shapes can be used.

In the cross-sectional view of the fastener 150 illustrated in FIG. 17A, the D-shaped channel 159 and the complimentary mid-section 123 is illustrated. As the mid-section 123 penetrates the internal channel 159 to enable rotation of the fastening device 150 the complimentary configurations must be correctly dimensioned. The cross-section F in FIG. 17B shows the complimentary relationship between the interior channel 159 and the mid-section 123 of the guide rod 120. When the insertion torque is transmitted through the guide rod 120, the guide rod rotates and interacts with the complimentary interior channel 159 of the fastening device 150. Ideally the radius of the guide rod 120 is such that less than 10 degrees of rotation occurs between the interior channel 159 and the guide rod 120. The gap 166 between the interior channel 159 and the guide rod mid-section 123 should provide torque transmission but not allow the guide rod 120 to rotate freely. The dimensions are depending upon the diameter of the guide rod and interior of the device however for optimal rotation, with the overall diameter of the rod being less than the distance from the center of the screw to the flat.

Figures 18A, 18B, 18C, 18D:
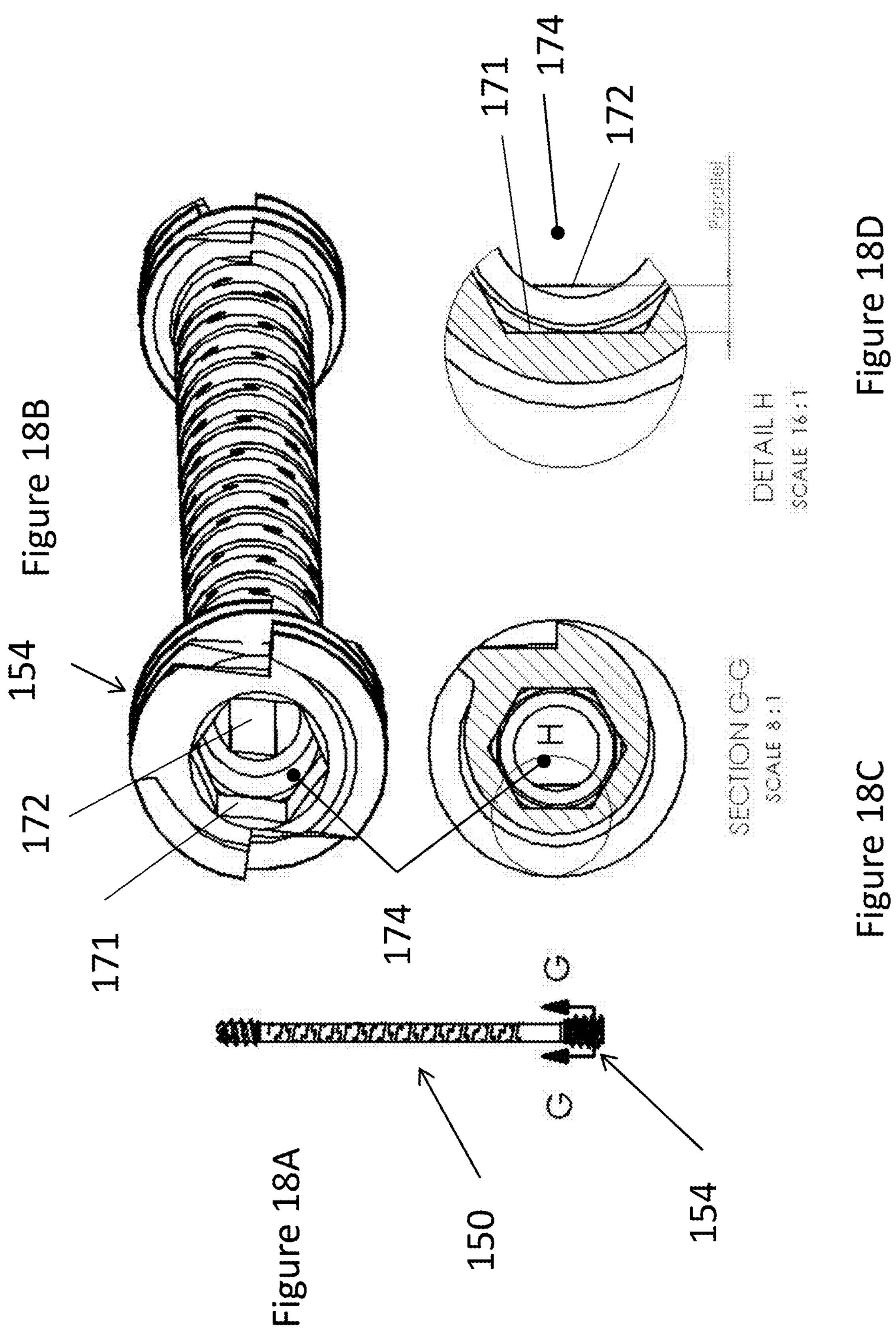
FIG. 18A illustrates the proximal end 554 of the flexible screw 150 in accordance with the invention.
FIG. 18B shows the interior of the proximal end of the screw illustrating the flats in accordance with the invention.
FIG. 18C shows the cross section of the receiving orifice of the screw in accordance with the invention.
FIG. 18D is a cross section illustrating the flat within the shaft of the screw in accordance with the invention.

FIG. 18A illustrates the screw 150 having a unique interior cross section that is complimentary to the cross-sectional shape of the guide rod 120 as well as indicating the location of the proximal segment 154 detail location G-G. The driver receiving orifice 174 in the proximal segment 154 is illustrated in FIG. 18B where a feature of the driver receiving orifice 174, such as the flat surface 172, is reproduced along the length of the interior of the shaft 180. Although the flat surface 172 does not have to run the entire length of the device, it is optimal that the interior flat surface 172 does run from the distal to proximal end along the interior of the shaft 180 to interact fully with the flat surface 130 of guide rod 120 or other inserting device.

In the illustrated example the flat surface 170 is one of the flat edges of the driver hexagon referenced to the flat surface 172 machined in linear alignment along the interior length of the body 180. This combination enables seamless contact between the guide rod 120 and the driver tool. It is also advantageous that the flat surface 170 is parallel or referenced to a landmark in the driving receiver orifice such as the flat surface 170 of the hexagonal driver receiver orifice 174.

FIG. 18C shows the cross-section G-G of FIG. 18A to illustrate the cross-sectional shape of the receiving orifice 174 which in this configuration is a common hexagonal shape. Other common types of driving orifices are known in the art.

FIG. 18D illustrates the detail view H in FIG. 18C to illustrate the flat surface 170 of the driver receiving orifice 174 that is complimentary to the flat surface 172 within the interior of the shaft 180 of the screw 150. These surfaces are referred to as alignment surfaces. In this application the flat surface 172 is manufactured to be parallel and in alignment to the flat surface 170. Using flat surfaces 170 and 172 are one example of configurations that can be used. For example, another application may be where the alignment surfaces are perpendicular to one another. The relationship between the surfaces in the screw 150 must be maintained in the associated tools.

It should be noted that the use of a tool having a hexagon, or other polygonal shape, can be used with the D-shaped screw interior and guide rod being of complimentary manufacture. Although possible other shapes can be used that prevent rotation and meet the criteria set forth herein however the manufacturing difficulty and cost will increase. The relationship between the driver receiving orifice and the complimentary feature running along the interior length of the shaft allows for much simpler and more controlled insertion.

If the alignment surface relationship is not controlled but random, then an allowance for this misalignment has to be taken into account in the instrumentation as described hereinafter with respect to FIG. 24.

FIGS. 19-21 illustrate the locking nut 270 containing threads 272 along section A-A. The locking nut 270 has a projection 274 that is dimensioned to fit and rotate within the proximal receptacle 155. The threads 272 are compatible with the threads 122 of the guide rod 120 and once the handle sub-assembly 200 removed guide rod locking nut 270 is threaded onto the threaded portion 122. The guide rod locking nut 270 is threaded down to the proximal end 154 of the fastening device 150, drawing the tapered end 125 of the guide rod 120 against the distal end 160 of the fastening device 150 to compress and stiffen the fastening device 150. Once firmly in place, the guide rod 120 is cut off proximal to the guide rod locking nut 270.

Figure 22:
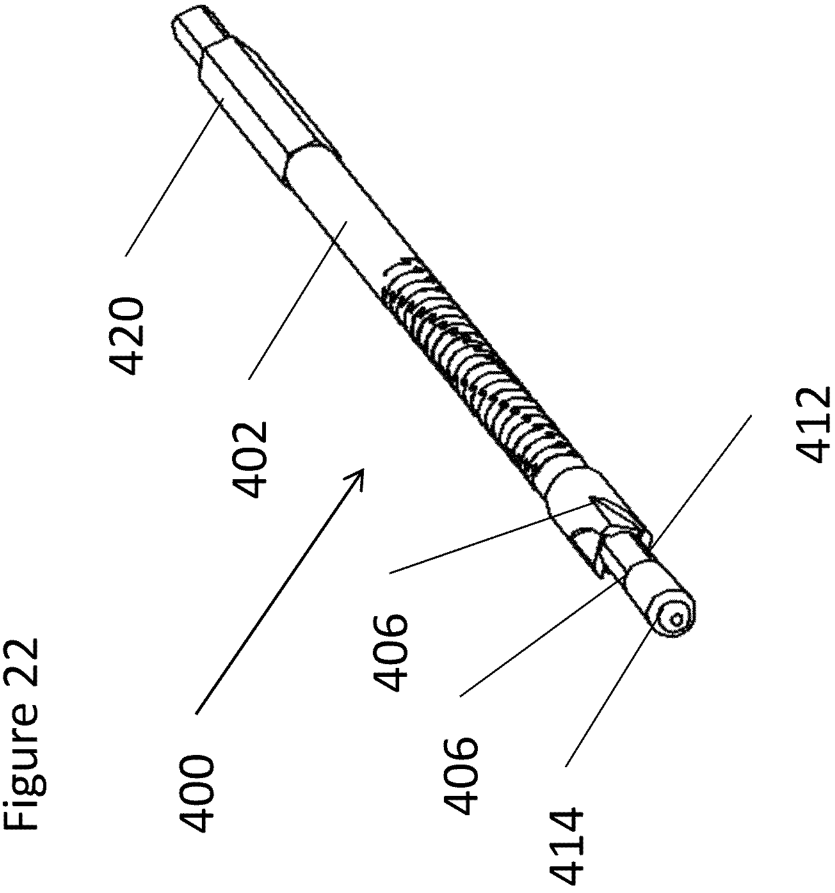
FIG. 22 is a perspective view of a reamer of in accordance with the invention.
Figures 23A, 23B, 23C:
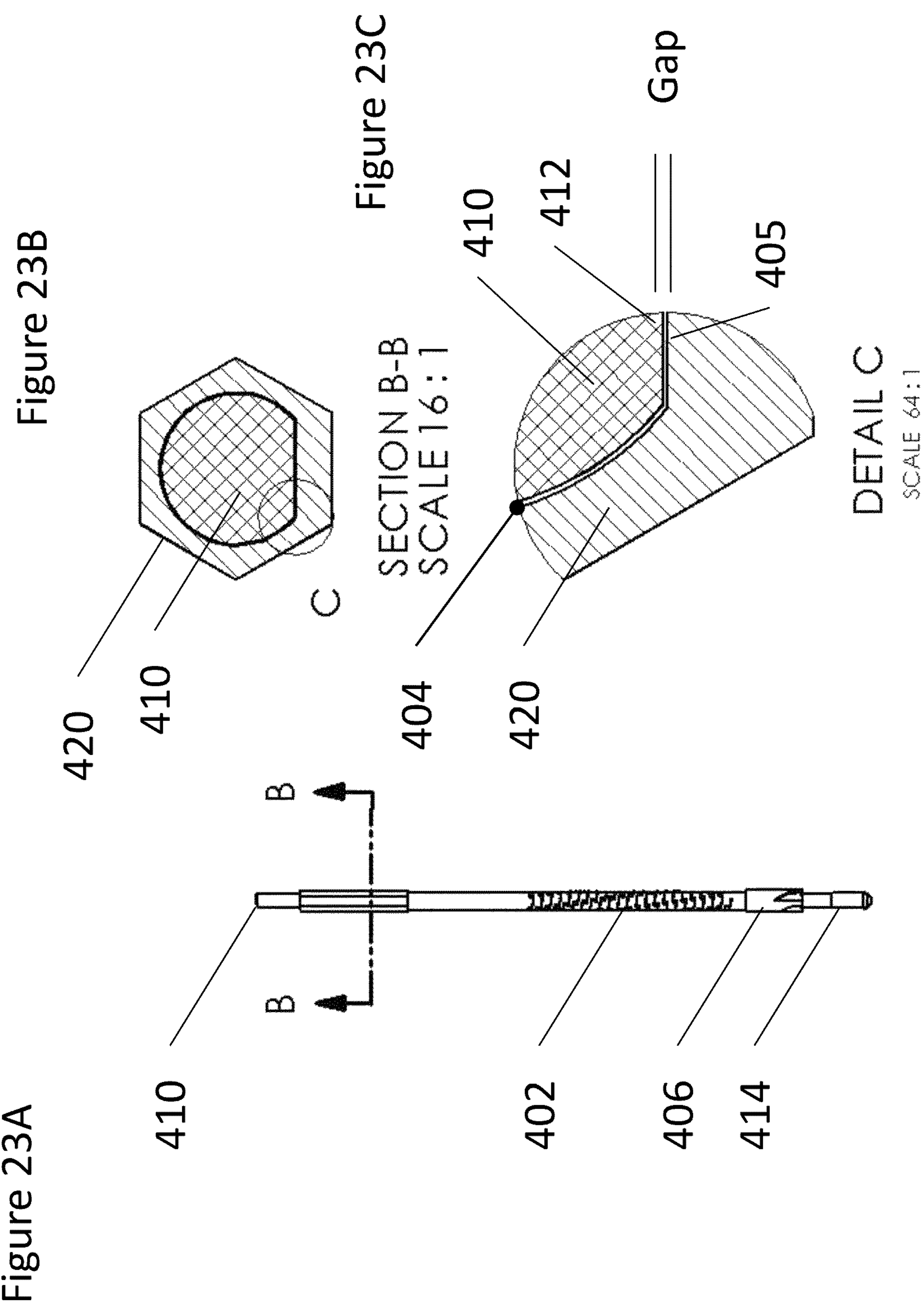
FIG. 23A illustrates a reamer 400 of the present invention showing locations for sectional view B-B.
FIG. 23B shows the cross-section B-B of the reamer 400 of FIG. 23A.
FIG. 23C shows details C of reamer 400 of FIG. 23B.

In FIG. 22 and FIG. 23A a reamer 400 is illustrated having a flexible mid shaft body 402 and distal cutting end 406. The reamer 400 has a D-shaped interior 404 (FIGS. 22B and 22C) that, when placed over a guide rod 410 with the complimentary D-shaped flat 412 fitting against the flat 405 of the D-shaped interior channel 404, enhances rotation between the reamer 400 and the guide rod 410. The distal end 414 of the guide rod 410 has, as disclosed previously, a diameter greater than the interior channel 404 of the reamer 400 to maintain the guide rod 410 within the reamer 400 during use and preventing the reamer 400 from going past the end of the guide rod 410. The proximal end 420 of the reamer 400 is configured to receive a driver such as a hand drill or other means known in the art. As disclosed heretofore, there are a number of complimentary cross-sectional configurations for both the guide rod 410 and the reamer 402 that can be used to maintain the guide rod 410 in position. The proximal end of the guide rod 410 is configured to receive a driver and can be any configuration compatible with the driver being used.

In these figures the reamer 400 is not fully positioned over the guide rod 410, extending slightly proximal to the distal tip 414 of the guide rod 410. Prior to reaming the guide rod 410 would be fully inserted into the bone to enable the reamer cutting edge 406 engage with the bone as the reamer is advanced down the guide rod 410. The distal tip 414 prevents the reamer 400 from traveling past the end of guide rod.

After reaming the bone, the reamer 400 is removed, leaving the guide rod 120 in place. The screw 150 is then inserted over the guide rod 120, following the reamed path.

In FIG. 23A the passage of the reamer 402 over the guide rod 410 is illustrated. The decrease in the distal end 414 to the guide rod 410 is also clearly seen as well as the location of section B-B, shown in detail in FIG. 22B.

FIG. 23C illustrates a cross section of location B-B and detail C, clearly shows the positioning between the guide rod 410 flat 412 and the reamer 400 flat 405. The dimensioning between the reamer 402 and the guide rod 410 are such that a slight space is left between the two elements as illustrated in FIG. 23C and disclosed heretofore. The dimensions between the radius of the guide rod 410 and the interior channel 404 will be dependent upon the overall diameters of the reamer and matching guide rod such that the guide rod cannot rotate freely within the reamer.

In some applications it is advantageous to use an extension bar when the device to be inserted is in a hard-to-reach location or further than the normal reach of the usual tool. Such an extension bar for the disclosed screw 150 is shown in FIG. 24 and FIGS. 25A-D.

Figure 24:
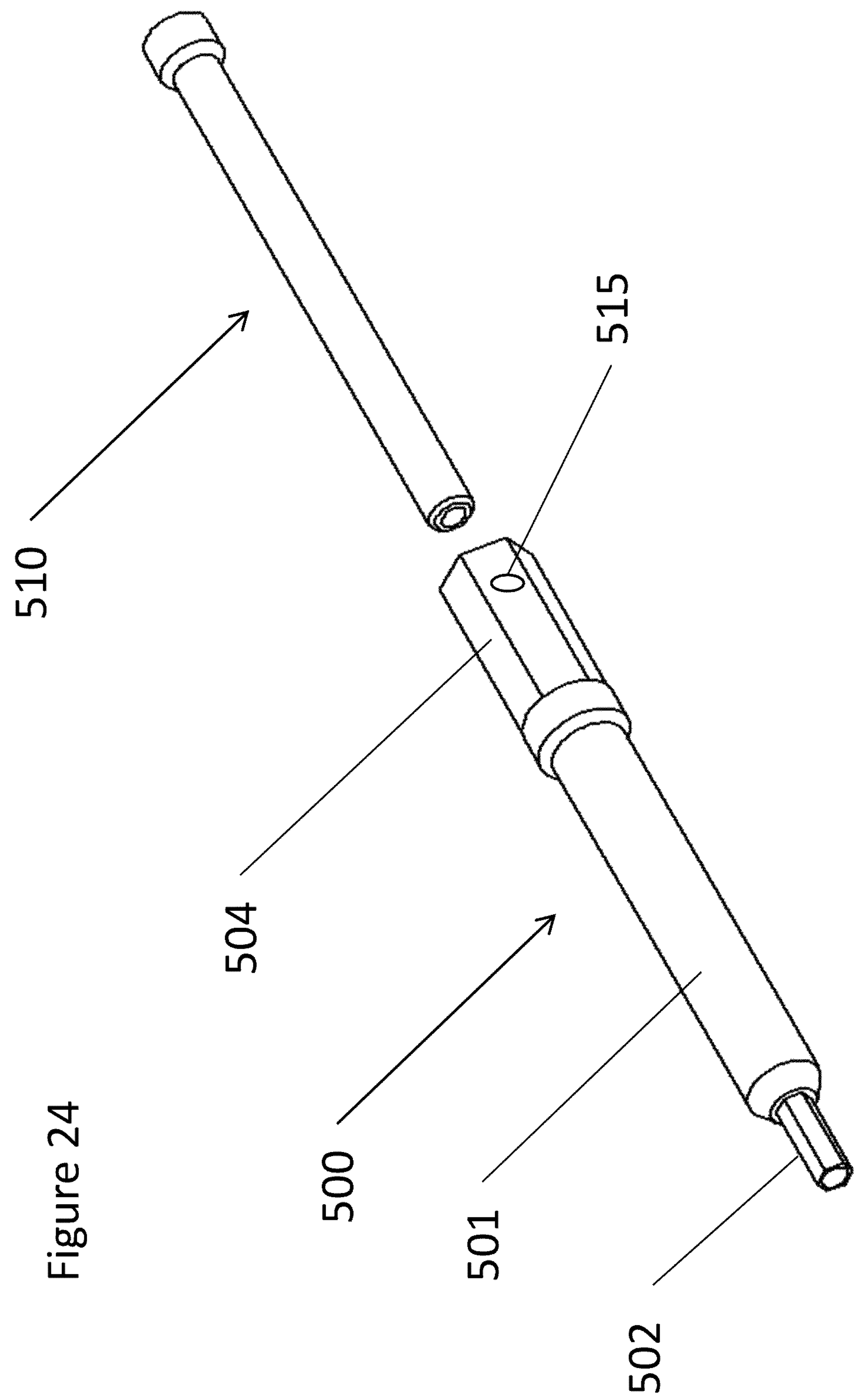
FIG. 24 illustrates an extension device 500 for aiding in the insertion of the screw 150 when additional length is required in accordance with the invention.

FIG. 24 illustrates an extension device 500 for aiding in the insertion of the screw 150 when additional length is required than is provided by the tool assembly 100. The extension shaft has a middle section 501, a distal tip 502 and proximal driving end 504. The proximal driving end 504 example illustrated contains a receiving hole 515 to receive a set screw and secure the inner sleeve 510. The distal tip 502 is configured to interact with the receiving orifice 174 of the screw 150 and would be substituted for the coupling mechanism 230 or other driver. The driving end 504 is configured to receive a suitable driver, such as the tool assembly 100 or other attachment and handle.

Figures 25A, 25B, 25C, 25D:
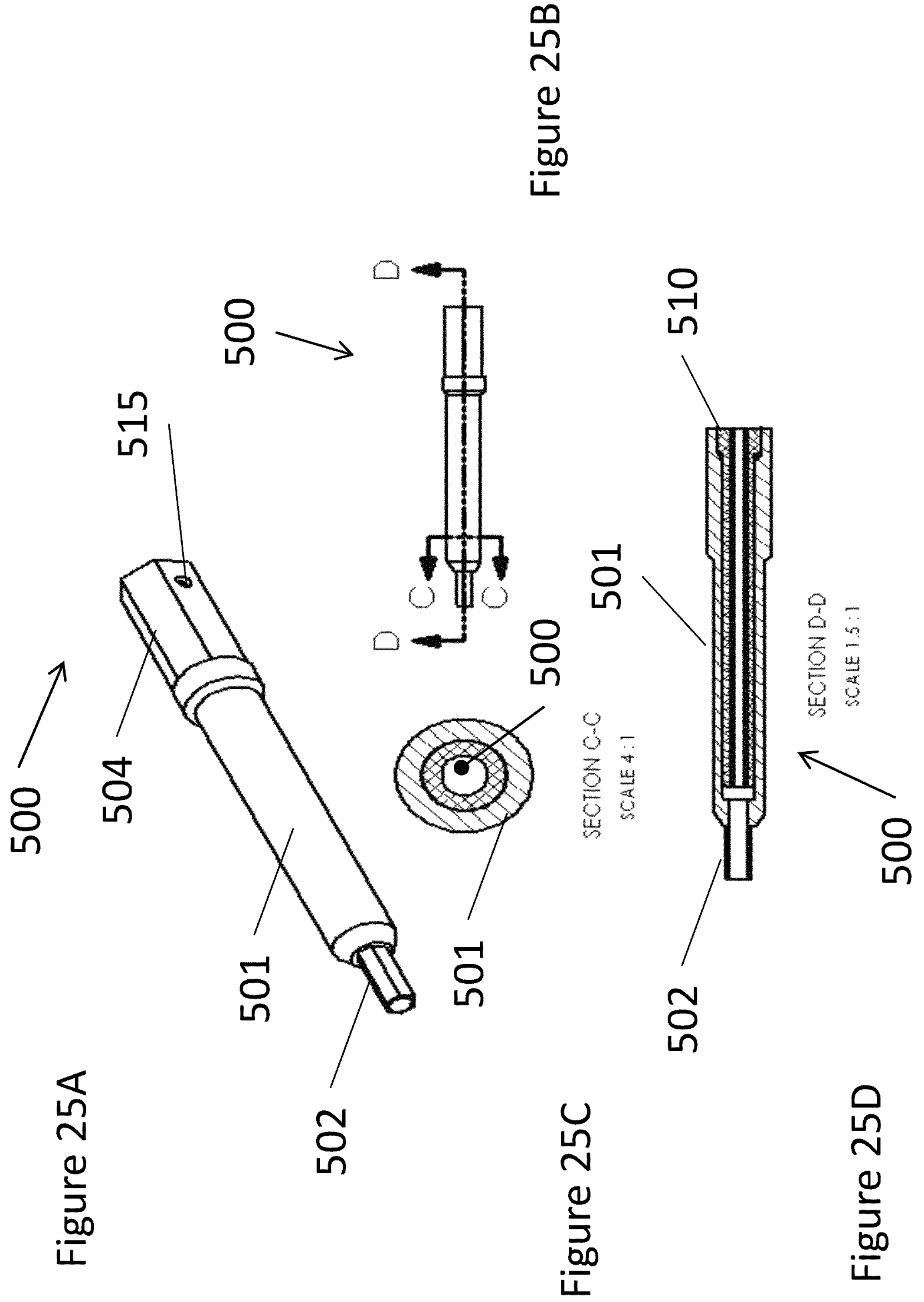
FIG. 25A illustrates the assembled extension device 500 in accordance with the invention.
FIG. 25B illustrates the extension device of FIG. 25A with the locations for sectional views C-C and D-D in accordance with the invention.
FIG. 25C shows the cross-section C-C with extension tube 500 and the inner sleeve 510 in accordance with the invention.
FIG. 25D shows the inner sleeve 510 within the extension tube 500 in accordance with the invention.

FIG. 25A illustrates the assembled extension device 500 with the inner sleeve 510 for aiding in the insertion of the screw 150, distal tip 502 for mating with the receiving orifice 174 of the screw 150, and proximal driving end 504 which is driven by a suitable handle. FIG. 25B shows the locations for sectional views C-C and D-D.

The guide rod alignment sleeve 510 is required when the alignment of the distal flat surface 170, or other distinct feature of the orifice 174, is not oriented with the flat 172 within the interior of the shaft 180 of the screw 150.

As illustrated in FIG. 25C the interior of the outer extension device 500 and the exterior periphery of the alignment sleeve 510 are circular, leaving the alignment sleeve 510 free to rotate within the outer extension device 500, thereby enabling the guide rod 120 to be aligned with the D-shaped interior of the screw 150. The interior cross-sectional shape 505 of the alignment sleeve 510 is complimentary to the outer periphery of the guide rod 120 illustrated heretofore.

In FIG. 25D the extension device 500 has been assembled and ready to insert the guide rod 120 (not illustrated). Once assembled, the distal tip 502 is inserted in the driving orifice 174 of the screw 150 and the alignment sleeve 510 is locked on place. The alignment sleeve 510 can be locked into place through the use of set screws, locking nuts or other means that will be known to those skilled in the art.

Figure 26:
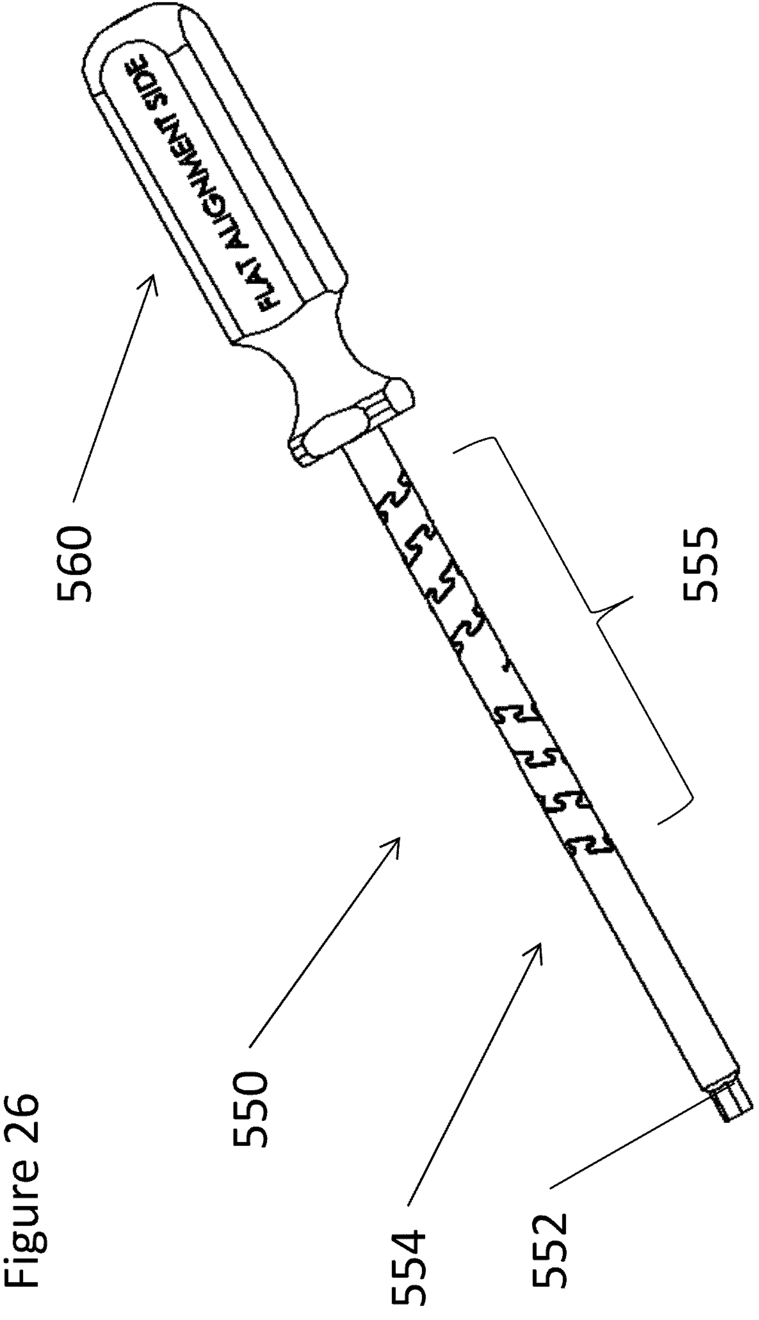
FIG. 26 illustrates a manual screwdriver 550 with a distal tip 552, an extension shaft 554 and a handle 560 in accordance with the invention.

FIG. 26 illustrates a manual screwdriver 550 with a distal tip 552, an extension shaft 554 and a handle 560. The extension shaft 554 illustrated has a flexible shaft segment 555, however the entire shaft can be rigid, depending upon user preference and end use. The shaft 554 can be either permanently attached to the handle 560 or inserted into the handle 560 for interchangeability of the shaft 550 for different sizes or shapes of the distal tip 552. The handle 560 in this and other figures is marked "Flat Alignment Side" or other notification to facilitate alignment of the flat 170 of the screw 150.

Figures 27A, 27B, 27C, 27D:
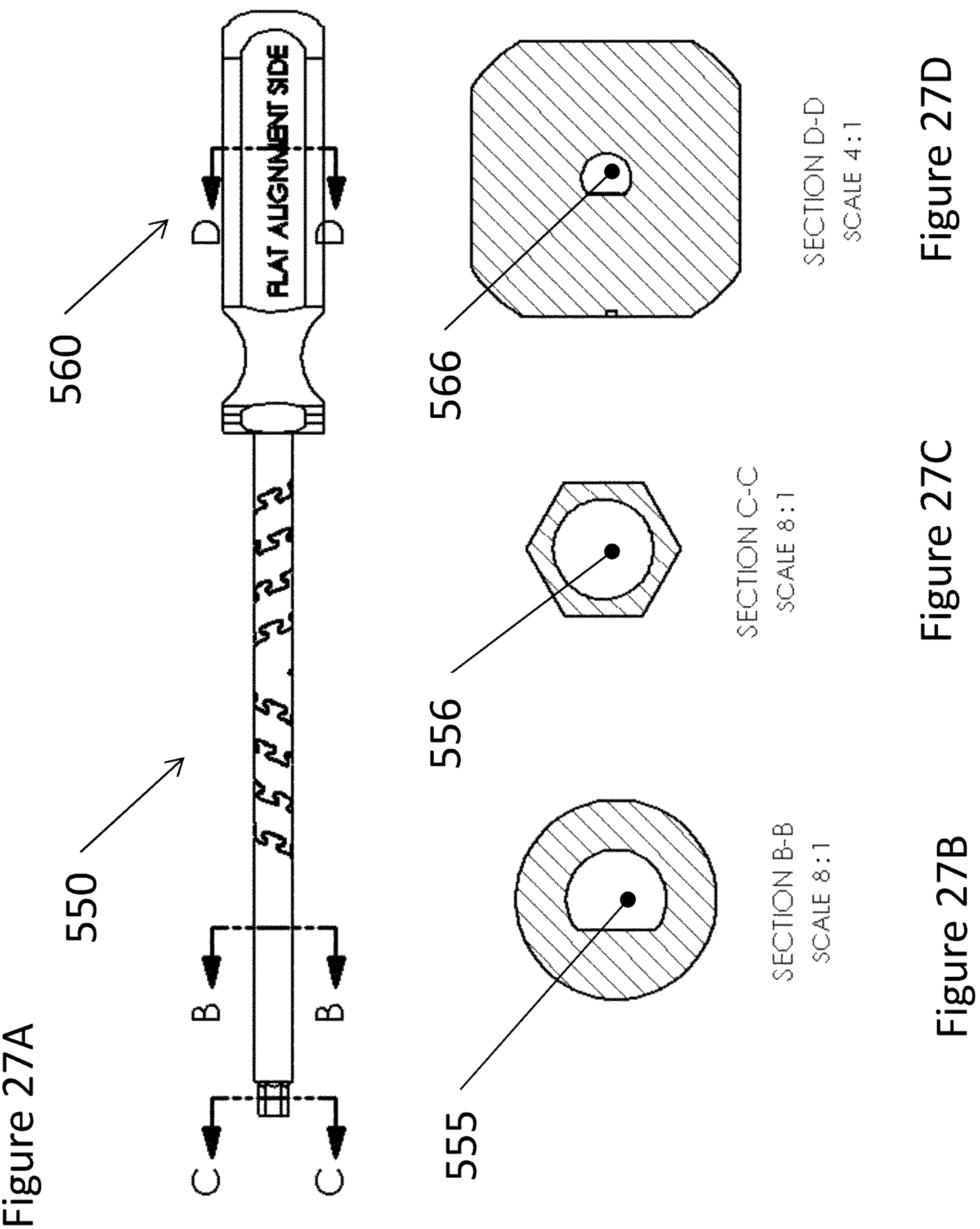
FIG. 27A illustrates the locations for sectional views B-B, C-C and D-D within the screwdriver of FIG. 26 in accordance with the invention.
FIG. 27B show the cross-sectional section B-B illustrating the flat within the shaft in accordance with the invention.
FIG. 27C show the cross-sectional section C-C illustrating the tip of the driver in accordance with the invention.
FIG. 27D show the cross-sectional section D-D of the handle in accordance with the invention.

FIG. 27A illustrates the screwdriver 550 indicating the locations for sectional views B-B, C-C and D-D. The cross-section B-B is illustrated in FIG. 27B to show the unique interior cross-sectional shape 555 that is complimentary to the outer shape of the guide rod 120 as shown in FIG. 7.

FIG. 27C shows the cross-sectional section C-C for illustration of the interior cross-sectional shape 556 that allows uninhibited passage of the guide rod 120 as shown in FIG. 7. Alternatively, the illustrated shape for the interior could be the continued unique interior cross-sectional shape 555 displayed in FIG. 27B.

FIG. 27D show the cross-sectional section D-D of the handle 560 for illustration of the interior cross-sectional shape 566 that is complimentary to the outer shape of the guide rod 120 as shown in FIG. 7 for a permanently attached shaft 550. Alternatively, the illustrated shape for the interior 566 can be the outer cross-sectional shape of the shaft displayed in FIG. 27B.

Figure 28:
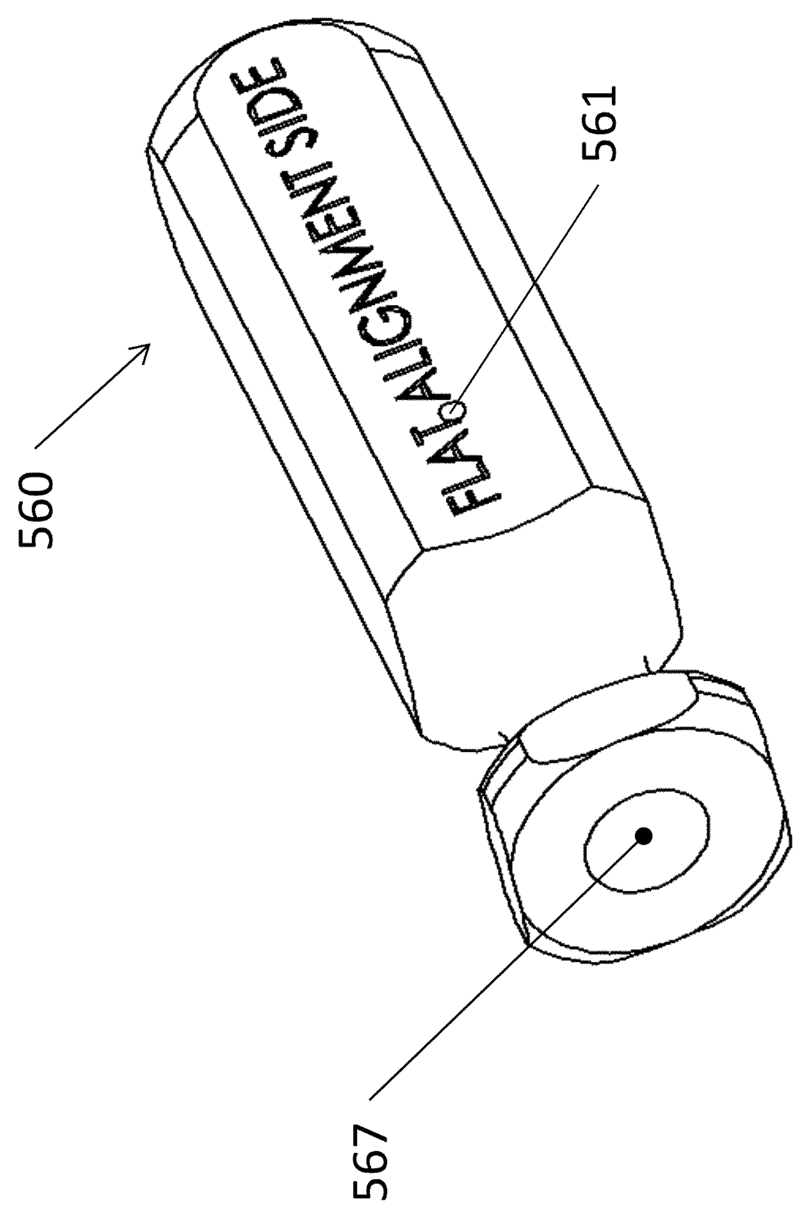
FIG. 28 illustrates the handle 560 with an orifice 567 for receiving a shaft 550 or extension 570 in accordance with the invention.
Figures 30A, 30B, 30C:
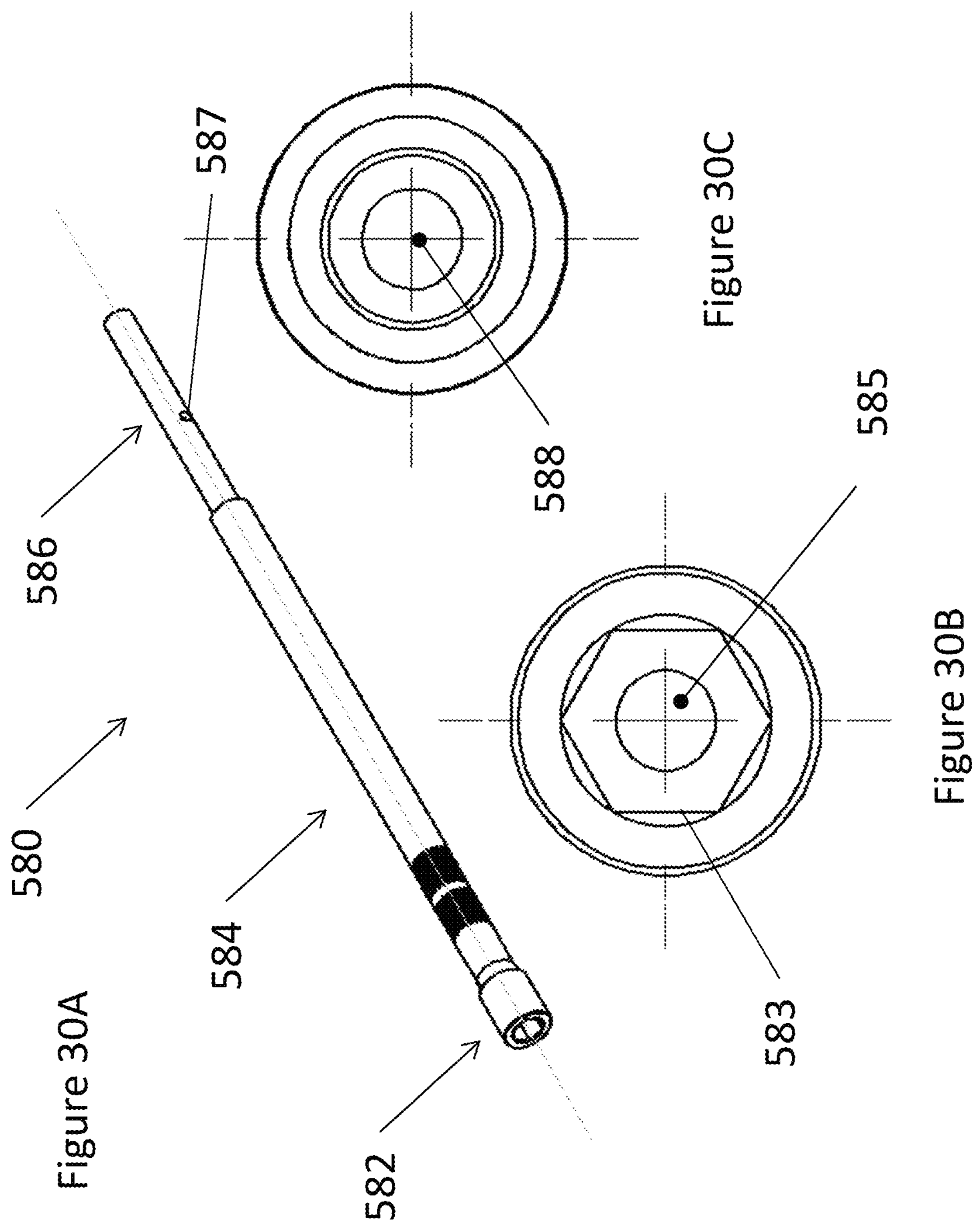
FIG. 30A illustrates an extension drive 580 for use with the handle 560 and the driver bit 570 in accordance with the invention.
FIG. 30B shows the distal end 582 of the extension drive of FIG. 30A in accordance with the invention.
FIG. 30C shows the proximal end 586 and the cannulated orifice 588 extending through the extension bar 580 in accordance with the invention.

The handle 560 is illustrated in more detail in FIG. 28 illustrating the orifice 567 for receiving a shaft 554 (FIG. 26) or an extension 580 as illustrated in FIG. 30A. A hole 561 is provide for alignment and locking with the extension drive 580 via the alignment and locking hole 587 using a commonly known in the art, set screw.

Figures 29A, 29B:
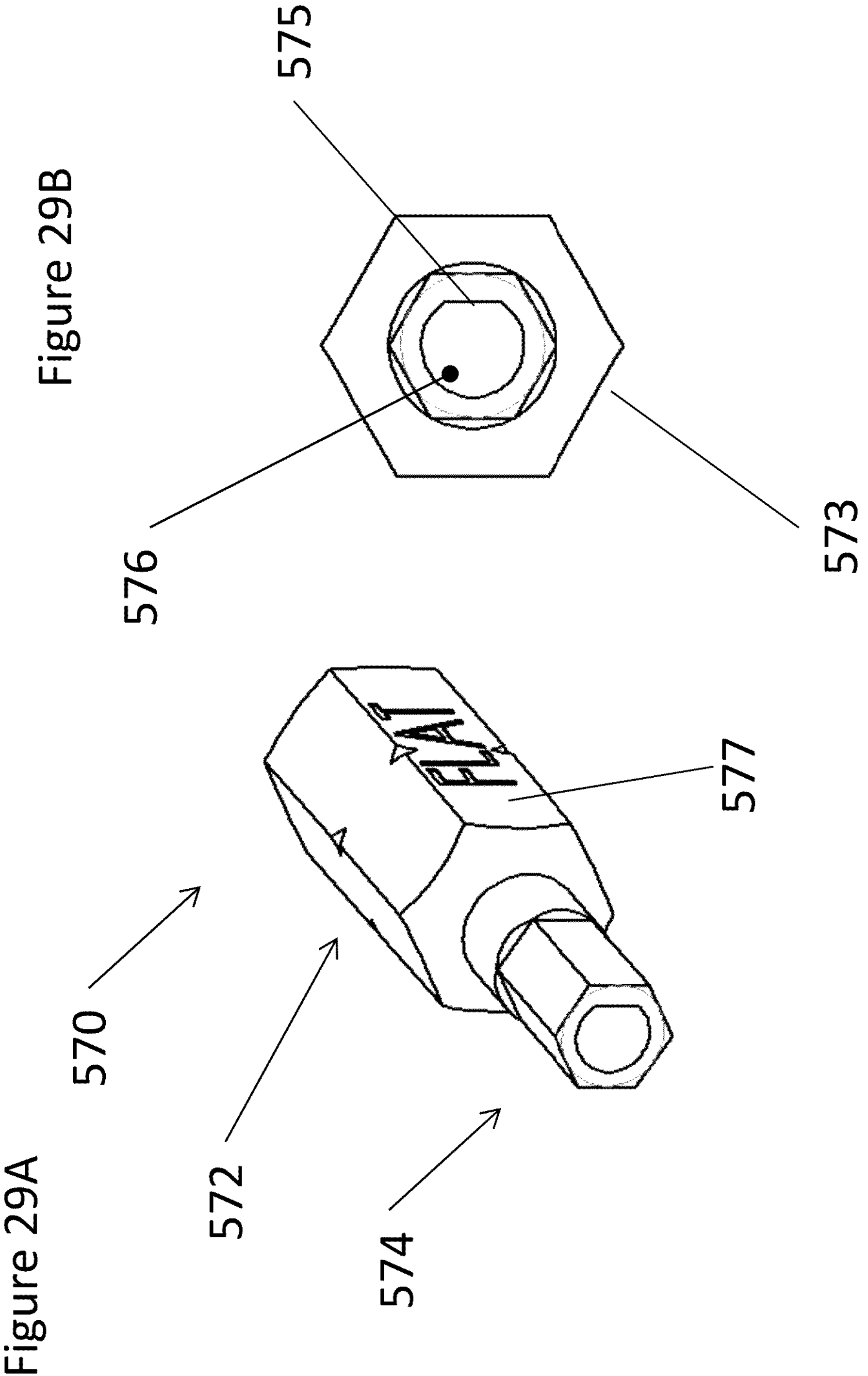
FIG. 29A illustrates a driver bit 570 with a hex style drive end 574 and a hexagonal bit shank 572 in accordance with the invention.
FIG. 29B illustrates a central cannula 576 complimentary to the exterior cross sectional shape of the guide rod 120 in accordance with the invention.

FIGS. 29A-B illustrate a driver bit 570 with a hex style drive end 574 and a bit shank 572. In this example the bit shank is shown with a hexagonal shape 573 although other shapes as known in the art can be used. The central cannula 576 is configured with an alignment face 575 and shape complimentary to the exterior cross-sectional shape of the guide rod 120. In order to facilitate use, the side of the bit that is in alignment with the interior flat 575 is marked with an indicator, in this example "FLAT" 577.

FIG. 30A illustrates an extension drive bar 580 for use with the handle 560 (FIG. 28) and the driver bit 570 (FIGS. 29A-B). The extension drive 580 is comprised of the drive attachment shaft 586, the main body 584 and the bit attachment end 582. For illustrative purpose, the bit attachment 582 is shown with the most commonly used hexagonal shaped attachment interior shape 583. The extension drive 580 has a central cannula 588 that allows for its passage over the guide rod 120. The drive attachment shaft 586 has an alignment and locking hole 587 for mating with the handle 560 using a set screw.

FIG. 30B shows the distal end 582 with a commonly used hexagonal shaped attachment interior shape 583 and the internal cavity 585.

FIG. 30C shows the proximal end 586 and the cannulated orifice 588 extending through the extension drive bar 580.

Socket extension drives are used with sockets and hand drive tools to tighten and loosen fasteners. They connect between the drive end of the hand tool and the drive end of the socket to lengthen the reach of the tool so it can access fasteners in hard-to-reach locations.

Figure 31:
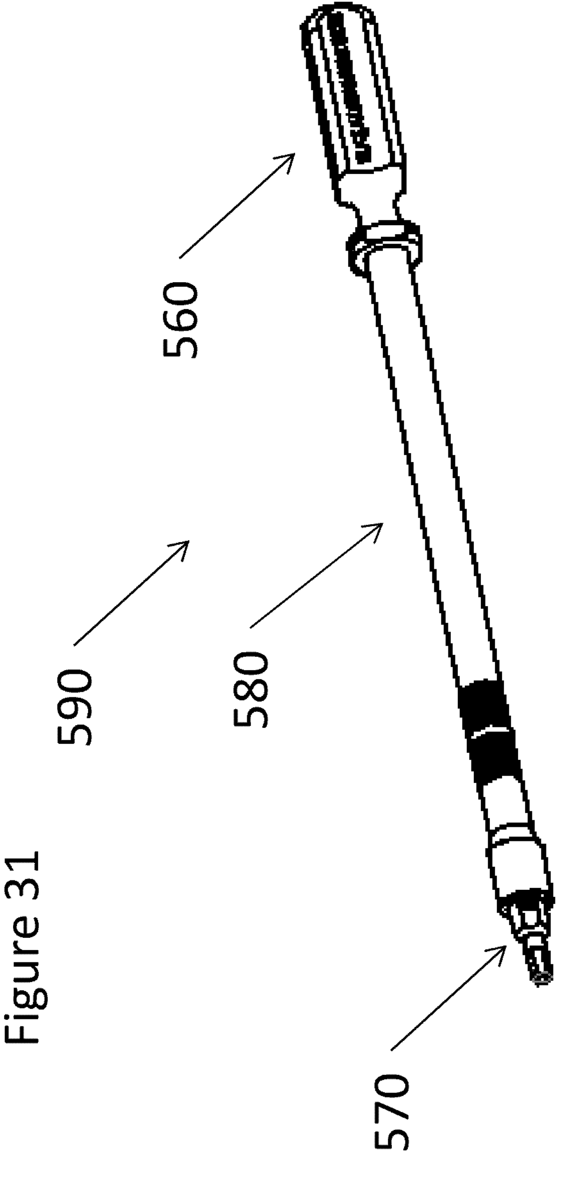
FIG. 31 illustrates the assembled insertion tool 590 comprised of the extension drive 580 with the handle 560 and the driver bit 570 in accordance with the invention.

FIG. 31 illustrates the assembled insertion tool 590 comprised of the extension drive bar 580 with the handle 560 and the driver bit 570.

Figure 32:
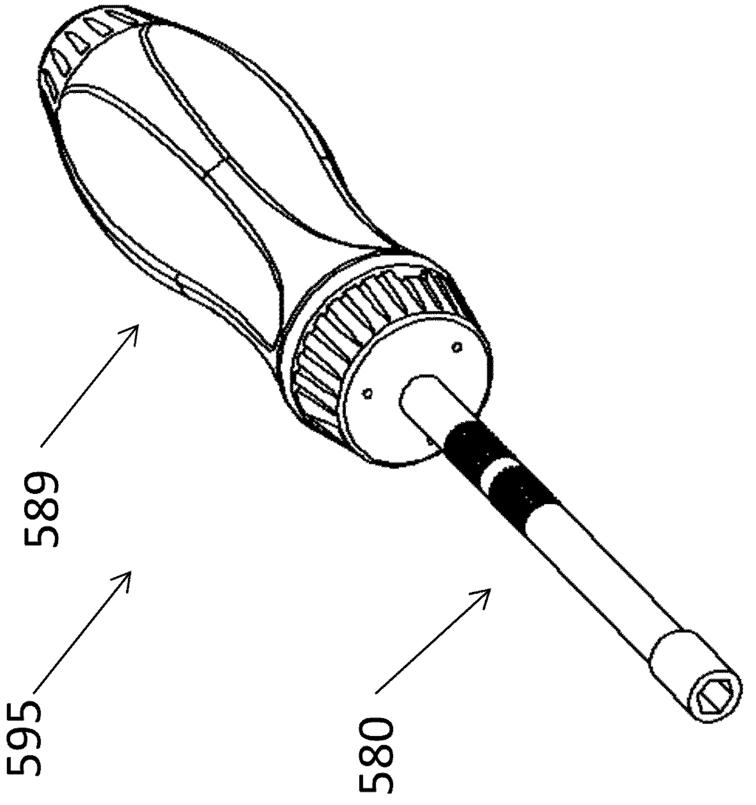
FIG. 32 illustrates the application using a ratcheting handle 595 including the extension 580 with a ratchet handle 589 in accordance with the invention.

FIG. 32 illustrates the application using a ratcheting handle 595 including the extension 580 with a ratchet handle 589 for faster insertion.

Figure 33:
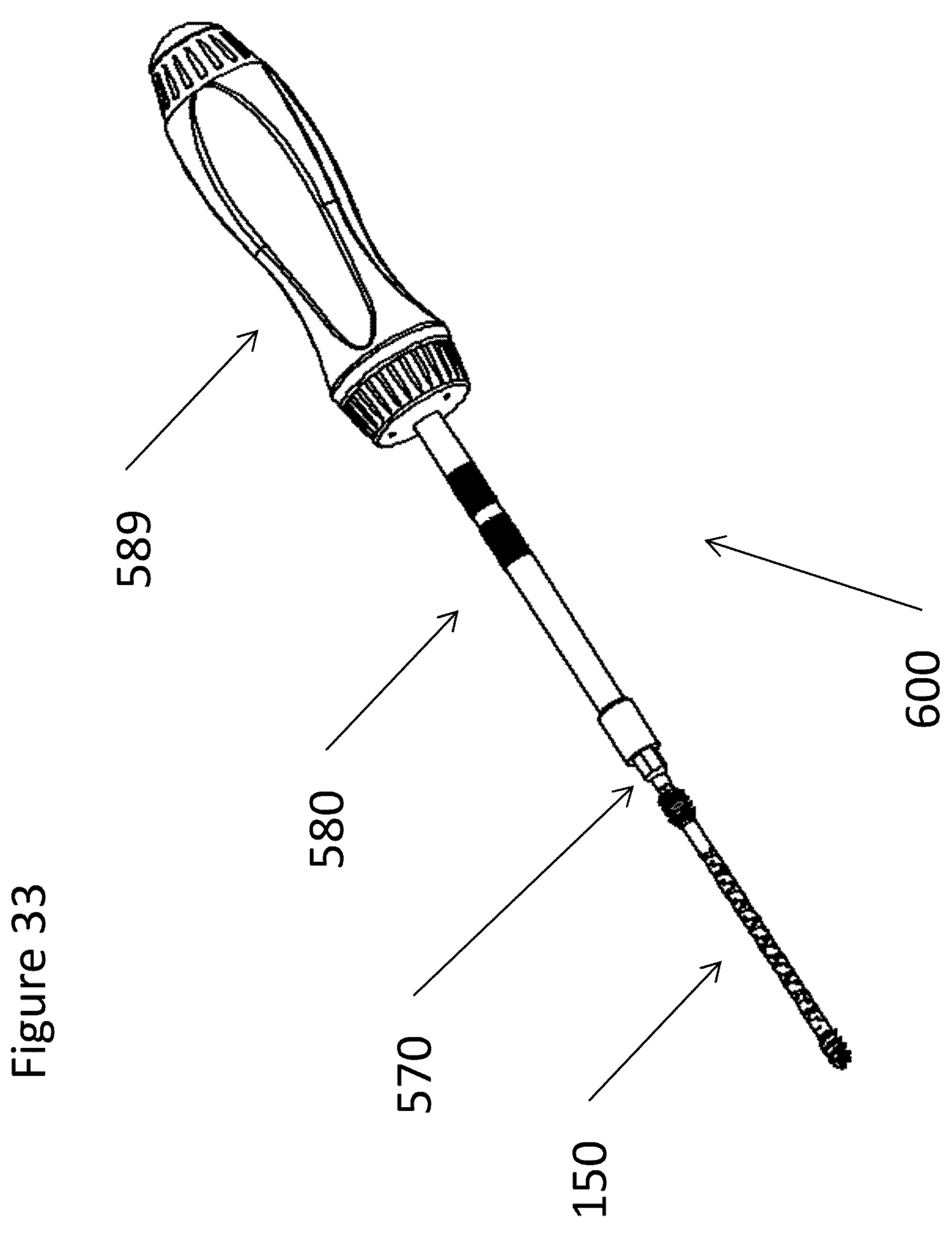
FIG. 33 illustrates an assembled insertion unit 600 comprised of the screw 150, the drive bit 570, the extension rod 580 and the ratchet handle 589 in accordance with the invention.

FIG. 33 illustrates an assembled insertion unit 600 comprised of the screw 150, the drive bit 570, the extension rod 580 and the ratchet handle 595 which would be placed over the guide rod 120 for insertion into the bone.

Figures 34A, 34B, 34C, 34D, 34E:
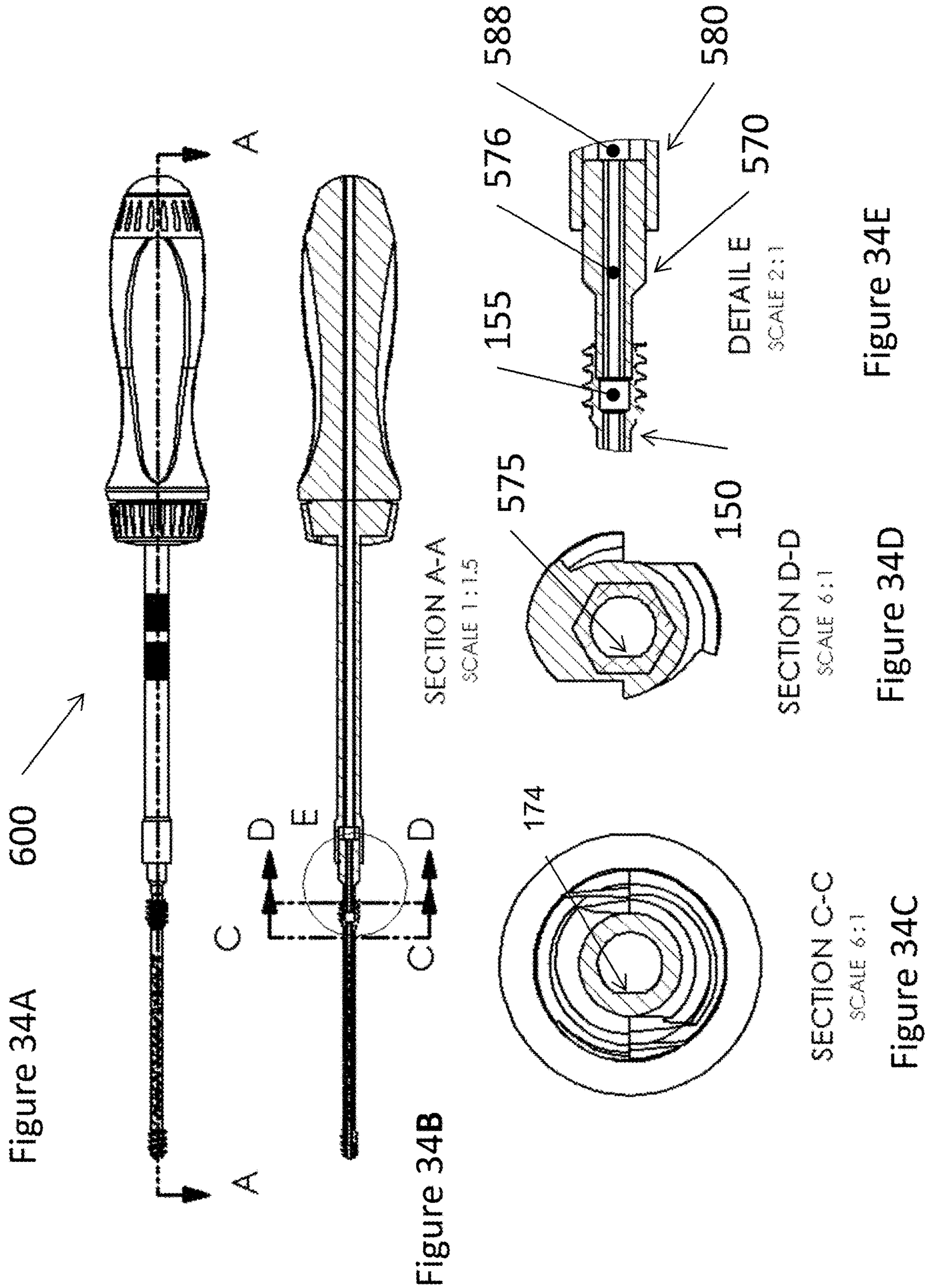
FIG. 34A illustrates an assembled insertion unit 600 in accordance with the invention.
FIG. 34B shows the sectional view A-A in accordance with the invention.
FIG. 34C shows the cross section of the screw 150 with the alignment surface 130 in accordance with the invention.
FIG. 34D shows the cross section of the hex bit 570 with the alignment surface 575 parallel to alignment surface 130 of the screw 120 in accordance with the invention.
FIG. 34E shows the detail view E with the cannula of the screw 155, hex bit 576 and extension rod 588 in accordance with the invention.

FIG. 34A illustrates an assembled insertion unit 600 comprised of the screw 150, the drive bit 570, the extension rod 580 and the ratchet handle 595 with section A-A shown to display the differences in cross sectional shapes of the attachment area.

FIG. 34B shows the sectional view A-A for describing the location of sections C-C and D-D and detail view E.

FIG. 34C shows the cross-section C-C of the screw 150 with the alignment surface 172.

FIG. 34D shows the cross-section D-D of the hex bit 570 with the alignment face 575 parallel to alignment surface 172 of the screw 150.

FIG. 34E shows the detail view E with the cannula of the screw 150, central cannula 576 and extension rod 588.

Figure 35:
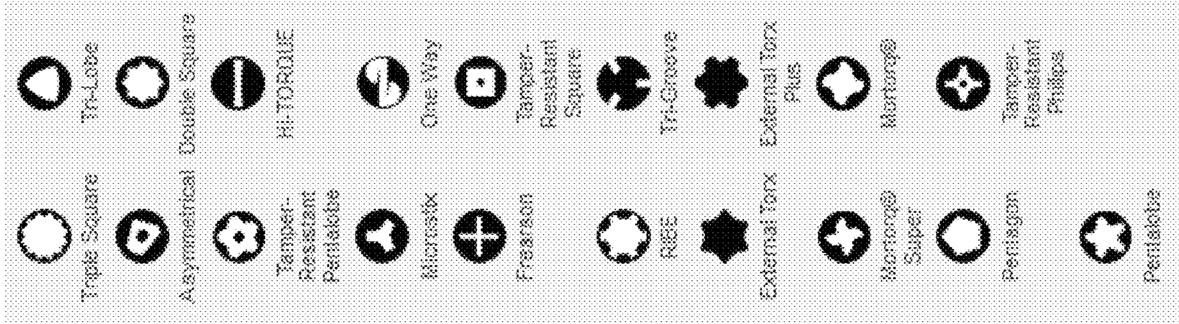
FIG. 35 illustrates examples of various driver configurations available in the commercial market.
Figure 35:
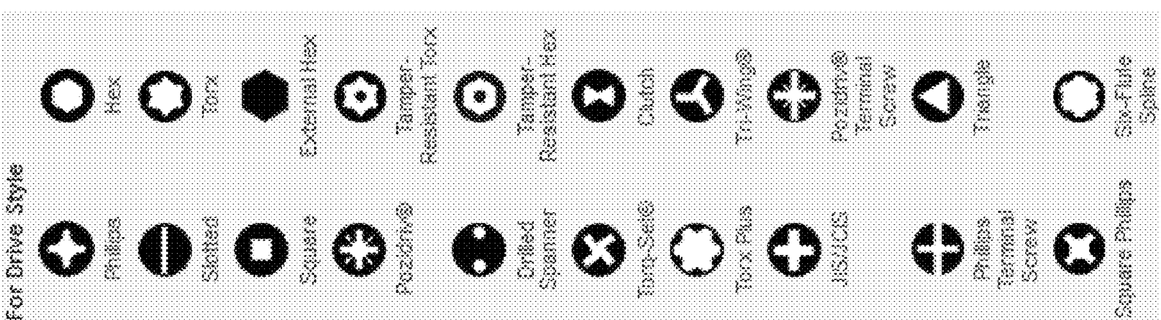

FIG. 35 illustrates the different driver bit 570 with a hex style drive end 574 provided by commercial industrial supply companies.

Method of Use

In the following description regarding use of the disclosed system, the repair of a fractured clavicle is being described, however that is for example only. In use, once an initial guide wire is passed through the fracture site, the clavicle is reamed to the appropriate diameter. The disclosed flexible guide rod 120 is passed past the fracture site and the fastening device 150, which has been attached to the handle sub-assembly 200, is inserted over the guide rod 120. The guide rod 120 has been locked in place within the handle sub assembly 100 as described heretofore. Due to the D-shaped configurations of the guide rod 120 and the interior channel 159 of the fastening device 150, the insertion can only be accomplished when the two elements are in alignment. Once the fastener has been screwed into the clavicle past the fracture site and firmly imbedded in the distal segment, the handle sub-assembly 200 is removed.

As the guide rod 120 must be longer than the fastening device 150 to allow for connection of the handle sub-assembly 200, the remaining threaded segment 151 extends from the insertion point. The locking nut 270 is placed on the threaded segment 151 and screwed down to the head of the fastening device 150, slightly compressing the fastening device 150 and preventing bone ingrowth into the screw's proximal cavity. The remaining threaded segment 151 is then cut to a predetermine distance from the proximal end of the fastening device 150.

PARTS LISTING

100 tool assembly
110 guide rod sub-assembly
120 guide rod
121 proximal threaded section
122 threads
123 mid-section
125 tapered end section
130 flat
150 fastening device
152 flexible segment
154 proximal segment
158 proximal threads
156 distal segment
157 distal threads
159 interior channel
160 internal distal end
161 sleeve
162 internal change point
166 gap
170 flat surface
172 flat surface
174 driver receiving orifice
180 interior of the shaft
200 handle sub assembly
210 handle
220 handle shank
222 guide rod shank passage
230 coupling mechanism
244 holder shaft
245 guide rod shaft passage
250 guide rod holder clamp
254 guide rod hole
255 guide rod holder clamp screw
238 guide rod holder
270 locking nut
272 threads
274 projection
400 reamer
402 mid shaft body
406 distal cutting end
404 interior
405 flat
410 guide rod
412 flat
414 distal end
420 proximal end
500 extension device
501 middle section
502 distal tip
504 proximal driving end
505 cross sectional shape
510 alignment sleeve
550 screwdriver
552 distal tip
554 extension shaft
555 flexible shaft segment
556 cross sectional shape
560 handle
561 hold
566 cross section (handle)
570 driver bit
572 bit shank
573 hexagonal shape
574 drive end
575 alignment face
576 central cannula
580 extension drive
582 bit attachment
583 interior shape
584 main body
586 drive attachment shaft
587 locking hole
588 central cannula
590 insertion tool
595 ratcheting handle
600 insertion unit

What is claimed is:

1. A system for manipulating a rotational device comprising:

A. a driver having a handle and a coupling element, said coupling element having an internal configuration and an external configuration;

B. a flexible guide rod extending through said handle and said coupling element, said flexible guide rod comprising:

i. a length, ii. a first periphery, iii. a second periphery less than said first periphery, iv. a distal section having said first periphery, v. a mid-section having said second periphery, vi. a proximal threaded section having said second periphery, and vii. an external rod feature along at least a part of the length;

C. a rotational device having a body, said body comprising:

i. a length, ii. an exterior, iii. a distal end, and iv. an open interior channel, said open interior channel having:

a. a distal section having a periphery, said distal section periphery having a size at least as great as said first periphery of the flexible guide rod and being dimensioned to receive said second periphery of the flexible guide rod, b. a mid-section having a periphery dimensioned to receive second periphery of the flexible guide rod, c. a proximal section having a periphery configured to receive the external configuration of the driver coupling element, and d. an interior channel feature extending along at least a portion of the interior channel mid-section and the interior channel proximal section;

wherein said external rod feature of the flexible guide rod and said interior channel feature of said open interior channel of said rotational device are complimentary and non-rotational to enable rotation of the rotational device along the length; and wherein said periphery of said interior channel mid-section prevents the distal section of the guide rod from entering the mid-section of the interior channel of the rotational device after the distal section of the guide rod is received by the distal section of the interior channel.

2. The system of claim 1 wherein said external rod feature is a flat to form a D-shape and said internal channel feature is a flat to receive said external rod feature in a non-rotation manner.

3. The system of claim 1 wherein said rotational device is a screw.

4. The system of claim 1 wherein said rotational device is a reamer.

5. The system of claim 1 wherein said distal section of said guide rod and said distal section of said rotational device are tapered.

6. The system of claim 1 further comprising a transitional point within said rotational device distal section to prevent said distal section of said guide rod from entering said mid-section of said rotational device.

7. The system of claim 2 wherein said flat is between 25 to 75 percent of a radius of said guide rod.

8. The system of claim 1 wherein dimensioning of said second periphery of said guide rod and said periphery of said mid-section of said rotational device form a gap that allows less than 10 degrees of rotation.

9. The system of claim 2 wherein said flat within said interior channel mid-section and said flat within said proximal section are in linear alignment.

10. The system of claim 1 wherein said interior channel feature within said interior channel mid-section and said interior channel feature within said interior channel proximal section are in linear alignment.

11. The system of claim 1 wherein said external rod feature of said proximal section of said guide rod is complimentary to a portion of said periphery of said proximal section of said interior channel.

12. The system of claim 1 further comprising an extension device to extend the distance between said rotational device and said driver, said extension device having a distal tip, a middle section, a proximal driving end, and an alignment sleeve dimensioned to fit and be rotational within said extension device, said alignment sleeve having an interior feature complimentary to said external rod feature of said guide rod wherein said alignment sleeve can rotate within said extension device to align the internal channel feature of said rotational device and said driver and being locked in alignment.

13. A system for manipulating a rotational device comprising:

A. a driver having a handle and a coupling element, said coupling element having an internal configuration and an external configuration;

B. a flexible guide rod extending through said handle and said coupling element, said flexible guide rod comprising:

i. a length, ii. a first periphery, iii. a second periphery less than said first periphery, iv. a distal section having said first periphery, v. a mid-section having said second periphery, vi. a proximal threaded section having said second periphery, and vii. an external rod feature along at least a part of the length;

C. a compression screw having a body, said compression screw body comprising:

i. a length;

ii. an exterior;

iii. a distal end;

iv. an open interior channel having:

a. a compression screw distal section, said compression screw distal section periphery having a size at least as great as said first periphery of the flexible guide rod and being dimensioned to receive said second periphery of the flexible guide rod, b. a compression screw mid-section having a periphery dimensioned to receive said second periphery of the flexible guide rod, and c. a compression screw proximal section having a periphery configured to receive the external configuration of the driver coupling element;

d. a screw interior channel feature extending along at least a portion of the interior channel mid-section and the proximal section, said screw interior channel feature within said interior channel mid-section and said screw interior channel feature within said proximal section are in linear alignment; and D. a reamer having a body, said reamer body comprising:

i. a reamer length;

ii. a reamer exterior;

iii. a reamer distal end having cutting edges;

iv. an open interior reamer channel having:

a. a reamer distal section, said reamer distal section periphery having a size at least as great as said first periphery of the flexible guide rod and being dimensioned to receive said second periphery of the flexible guide rod, b. a reamer mid-section having a periphery dimensioned to receive said second periphery of the flexible guide rod, e. a reamer proximal section having a periphery configured to receive the external configuration of the driver coupling element, and c. a reamer interior channel feature extending along at least a portion of the interior channel mid-section;

wherein the external rod feature is complimentary and non-rotational with said screw interior channel feature and said reamer interior channel feature to enable rotation of the rotational device along its length; and wherein said periphery of said interior channel mid-section prevents the distal section of the guide rod from entering the mid-section of the interior channel of the rotational device after the distal section of the guide rod is received by the distal section of the interior channel.

14. The system of claim 13 wherein said feature is a flat to form a D-shape.

15. The system of claim 13 further comprising a transitional point within said reamer distal section to prevent said distal section of said guide rod from entering said mid-section of said reamer.

16. The system of claim 13 wherein said flat is between 25 to 75 percent of a radius of said guide rod.

17. The system of claim 1 wherein dimensioning of said second periphery of said guide rod and said fourth periphery of said mid-section of said reamer form a gap that allows less than 10 degrees of rotation.

18. A system for manipulating a rotational device comprising:

A. a driver having a handle and a coupling element, said coupling element having an internal configuration and an external configuration;

B. a flexible guide rod extending through said handle and said coupling element, said flexible guide rod comprising:

i. a length, ii. a first periphery, iii. a second periphery less than said first periphery, iv. a distal section having said first periphery, v. a mid-section having said second periphery, vi. a proximal threaded section having said second periphery, and vii. a guide rod flat along at least a part of the length forming a D-shape, said guide rod flat being between 25 to 75 percent of a radius of said guide rod;

C. a rotational device having a body, said body comprising:

i. a length, ii. an exterior, iii. a distal end, and iv. an open interior channel, said open interior channel having:

a. a distal section having a periphery, said distal section periphery having a size at least as great as said first periphery of the flexible guide rod and being dimensioned to receive said second periphery of the flexible guide rod, b. a mid-section having a periphery dimensioned to receive second periphery of the flexible guide rod, c. a proximal section having a periphery configured to receive the external configuration of the driver coupling element, and d. an interior channel flat along at least a portion of the mid-section and said proximal section said flat within said interior channel mid-section, said interior channel flat within said proximal section and said mid-section being in linear alignment, said interior channel flat being complimentary and non-rotational with said first guide rod flat to enable rotation of the rotational device along the length of the rotational device;

wherein said periphery of said interior channel mid-section prevents the distal section of the guide rod from entering the mid-section of the interior channel of the rotational device after the distal section of the guide rod is received by the distal section of the interior channel; and wherein dimensioning of said second periphery of said guide rod and said periphery of said mid-section of said rotational device form a gap that allows less than 10 degrees of rotation.

* * * * *